(12) United States Patent
Kordikowski et al.

(10) Patent No.: US 11,993,582 B2
(45) Date of Patent: May 28, 2024

(54) CRYSTALLINE FORMS OF A LTA4H INHIBITOR

(71) Applicant: Novartis AG, Basel (CH)

(72) Inventors: Andreas Kordikowski, Binningen (CH); Yanxiang Wu, Shanghai (CN)

(73) Assignee: Novartis AG, Basel (CH)

( * ) Notice: Subject to any disclaimer, the term of this patent is extended or adjusted under 35 U.S.C. 154(b) by 704 days.

(21) Appl. No.: 17/264,333

(22) PCT Filed: Jul. 29, 2019

(86) PCT No.: PCT/IB2019/056436
§ 371 (c)(1),
(2) Date: Jan. 29, 2021

(87) PCT Pub. No.: WO2020/026108
PCT Pub. Date: Feb. 6, 2020

(65) Prior Publication Data
US 2021/0300897 A1   Sep. 30, 2021

(30) Foreign Application Priority Data

Jul. 31, 2018 (WO) ................ PCT/CN2018/000278

(51) Int. Cl.
*C07D 401/12* (2006.01)
*A61K 31/4439* (2006.01)
*A61K 45/06* (2006.01)

(52) U.S. Cl.
CPC ........ *C07D 401/12* (2013.01); *A61K 31/4439* (2013.01); *A61K 45/06* (2013.01); *C07B 2200/13* (2013.01)

(58) Field of Classification Search
None
See application file for complete search history.

(56) References Cited

U.S. PATENT DOCUMENTS

2009/0118257 A1   5/2009   Jankowski et al.

FOREIGN PATENT DOCUMENTS

| EP | 0303478 A1 | 2/1989 |
| WO | 2004002409 A2 | 1/2004 |
| WO | 2015/092740 A1 | 6/2015 |

OTHER PUBLICATIONS

Braga, et al., Crystal Polymorphism and Multiple Crystal Forms, Struct Bond, Feb. 25, 2009, 25-50, 132.
Hilfiker, et al., Relevance of Solid-state Properties for Pharmaceutical Products, Polymorphism: in the Pharmaceutical Industry, 2006, 1-19, Chapter I.
Caira, Mino R., "Crystalline Polymorphism of Organic Compounds" Topics in Current Chemistry, vol. 198, p. 163-208 (pp. 164-166, section 3.2, p. 188), 1998.
Morissette, Sherry L et al.: "High-throughput crystallization: polymorphs, salts, co-crystals and solvates of pharmaceutical solids", Advanced Drug Delivery Reviews, 2004, vol. 56, pp. 275-300.
Mit'Kina, E.L. et al. "Stress studies and photostability as part of pharmaceutical drug development data," Scientific Centre for Expert Evaluation of Medicinal Products, Moscow, 2015 (2): 9-12 Abstract.
Variankaval, Narayan et al., "From form to function: Crystallization of active pharmaceutical ingredients," AIChE, 2008, vol. 54(7), pp. 1682-1688, specifically see p. 1682 "Crystal Form".
Rodriguez-Spong, Barbara et al.: "General principles of pharmaceutical solid polymorphism: a supramolecular perspective", Advanced Drug Delivery Reviews, vol. 56, pp. 241-274, 2004.
Bernstein J., "Polymorphism of Molecular Crystals", New York: Oxford Univ. Press, 2002; Moscow: Nauka, Chapter 7.3.2: Biodostupnost (Bioavailability), pp. 324-330) 2007, Translation.
Bastin, et al., Salt Selection and Optimisation Procedures for Pharmaceutical New Chemical Entities, Organic Process Research & Development, 2000, 427-435, 4(5).
Grant, Theory and Origin of Polymorphism, Polymorphism in Pharmaceutical Solids, 1999, 1-33, chapter 1.
Guillory, Generations of Polymorphs, Hydrates, Solvates, and Amorphous Solids, Polymorphism in Pharmaceutical Solids, 1999, 51 pages, ed. Brittain, Marcel Dekker, New York.
Khankari, et al., Pharmaceutical hydrates, Thermochimica Acta, 1995, 61-79, 248.
Morris, Structural Aspects of Hydrates and Solvates, Polymorphism in Pharmaceutical Solids, 1999, 125-181.

*Primary Examiner* — Joseph R Kosack
(74) *Attorney, Agent, or Firm* — Francine F. Li

(57) ABSTRACT

This application relates to various crystalline forms of (S)-3-amino-4-(5-(4-((5-chloro-3-fluoropyridin-2-yl)oxy)phenyl)-2H-tetrazol-2-yl)butanoic acid in its free form, as well as compositions, method of making and methods of using the same. In some embodiments the crystalline forms also contain water ("hydrates"). These materials are useful in the treatment of diseases and disorders which are typically ameliorated by the inhibition of LTA4H. Such diseases and disorders may include inflammatory and autoimmune disorders and pulmonary and respiratory tract inflammation.

16 Claims, 6 Drawing Sheets

CRYSTALLINE FORMS OF A LTA4H INHIBITOR

This application is a U.S. national Phase filing of International Serial No. PCT/IB2019/056436 filed Jul. 29, 2019, and claims priority to PCT application serial No. PCT/CN2018/000278 filed Jul. 31, 2018, the content of which is incorporated herein by reference in their entirety.

FIELD OF INVENTION

The present disclosure generally relates to crystalline forms of (S)-3-amino-4-(5-(4-((5-chloro-3-fluoropyridin-2-yl)oxy)phenyl)-2H-tetrazol-2-yl)butanoic acid. The present disclosure also generally relates to a pharmaceutical composition comprising the crystalline forms, as well as methods for obtaining such crystalline forms and methods of using such crystalline forms in the treatment of diseases and disorders which are typically ameliorated by the inhibition of LTA4H. Such diseases and disorders may include inflammatory and autoimmune disorders and pulmonary and respiratory tract inflammation.

BACKGROUND (S)-3-amino-4-(5-(4-((5-chloro-3-fluoropyridin-2-yl)oxy)phenyl)-2H-tetrazol-2-yl)butanoic acid was first disclosed as an HCl salt in WO2015/092740, filed Dec. 18, 2014, which is incorporated by reference in its entirety, and is a LTA4H inhibitor having the structure of Formula (I):

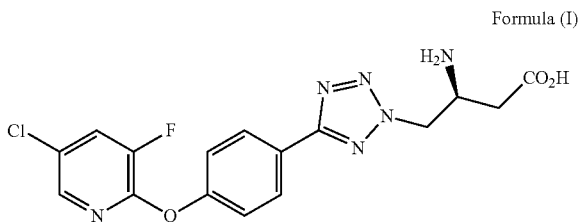 [SMILES: N[C@@H](CC(=O)O)Cn1nnc(-c2ccc(Oc3ncc(Cl)cc3F)cc2)n1]

Formula (I)

The compound of Formula (I) is useful in treating diseases and disorders which are typically ameliorated by the inhibition of LTA4H. Such diseases and conditions includes inflammatory and autoimmune disorders and pulmonary and respiratory tract inflammation.

Accordingly, the compound of Formula (I) is useful in the treatment of the following diseases or disorders: acute or chronic inflammation, anaphylactic reactions, allergic reactions, atopic dermatitis, psoriasis, acute respiratory distress syndrome, immune complex-mediated pulmonary injury and chronic obstructive pulmonary disease, inflammatory bowel diseases (including ulcerative colitis, Crohn's disease and post-surgical trauma), gastrointestinal ulcers, neutrophilic dermatoses (including but not limited to Pyoderma gangrenosum, Sweet's syndrome, acne and neutrophilic urticaria), immune-complex-mediated glomerulonephritis, autoimmune diseases (including insulin-dependent diabetes mellitus, multiple sclerosis, rheumatoid arthritis, osteoarthritis and systemic lupus erythematosus), vasculitides (including but not limited to cutaneous vasculitis, Behcets disease and Henoch Schonlein Purpura), cardiovascular disorders (including, but not limited to hypertension, atherosclerosis, aneurysm, critical leg ischemia, peripheral arterial occlusive disease, pulmonary artery hypertension and Reynaud's syndrome), sepsis, inflammatory and neuropathic pain including arthritic pain, periodontal disease including gingivitis, ear infections, migraine, benign prostatic hyperplasia, Sjogren-Larsson Syndrome and cancers (including, but not limited to, leukemias and lymphomas, prostate cancer, breast cancer, lung cancer, malignant melanoma, renal carcinoma, head and neck tumors and colorectal cancer).

Compound of Formula (I) is especially useful in the treatment of acute or chronic inflammation especially auto-inflammatory disorders such assterile neutrophilic inflammatory disorders, inflammatory bowel disease (including ulcerative colitis and Crohn's disease), neutrophilic dermatoses (including Pyoderma gangrenosum and acne), vasculitides, rheumatoid arthritis, gout and cardiovascular diseases.

Solid state form of the active pharmaceutical ingredient (API) of a particular drug is often an important determinant of the drug's ease of preparation, hygroscopicity, stability, solubility, storage stability, ease of formulation, rate of dissolution in gastrointestinal fluids and in vivo bioavailability. Crystalline forms occur where the same composition of matter crystallizes in a different lattice arrangement resulting in different thermodynamic properties and stabilities specific to the particular crystalline form. Crystalline forms may also include different hydrates or solvates of the same compound. In deciding which form is preferable, the numerous properties of the forms are compared and the preferred form chosen based on the many physical property variables. It is entirely possible that one form can be preferable in some circumstances where certain aspects such as ease of preparation, stability, etc. are deemed to be critical. In other situations, a different form may be preferred for greater dissolution rate and/or superior bioavailability.

Therefore, this ability of a chemical substance to crystallize in more than one crystalline form can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown crystalline form during manufacture can have a significant impact.

It is not yet possible to predict whether a particular compound or salt of a compound will form polymorphs, whether any such polymorphs will be suitable for commercial use in a therapeutic composition, or which polymorphs will display such desirable properties.

SUMMARY

The present disclosure provides crystalline forms of (S)-3-amino-4-(5-(4-((5-chloro-3-fluoropyridin-2-yl)oxy)phenyl)-2H-tetrazol-2-yl)butanoic acid in a free form (i.e. a non-salt form). In a particular embodiment, the free form further includes water (referred to herein as hydrate).

The present disclosure therefore provides a crystalline form of (S)-3-amino-4-(5-(4-((5-chloro-3-fluoropyridin-2-yl)oxy)phenyl)-2H-tetrazol-2-yl)butanoic acid in a free form.

The present disclosure further provides a crystalline form of a hydrate of (S)-3-amino-4-(5-(4-((5-chloro-3-fluoropyridin-2-yl)oxy)phenyl)-2H-tetrazol-2-yl)butanoic acid.

Embodiments of these crystalline forms include those forms designated herein as Form B and Form $H_B$. The names used herein to identify a specific form, e.g. "Form B" or "Form H$_B$, should not be considered limiting with respect to any other substance possessing similar or identical physical and chemical characteristics, but rather it should be understood that these designations are mere identifiers that should be interpreted according to the characterization information also presented herein.

Figure 1:
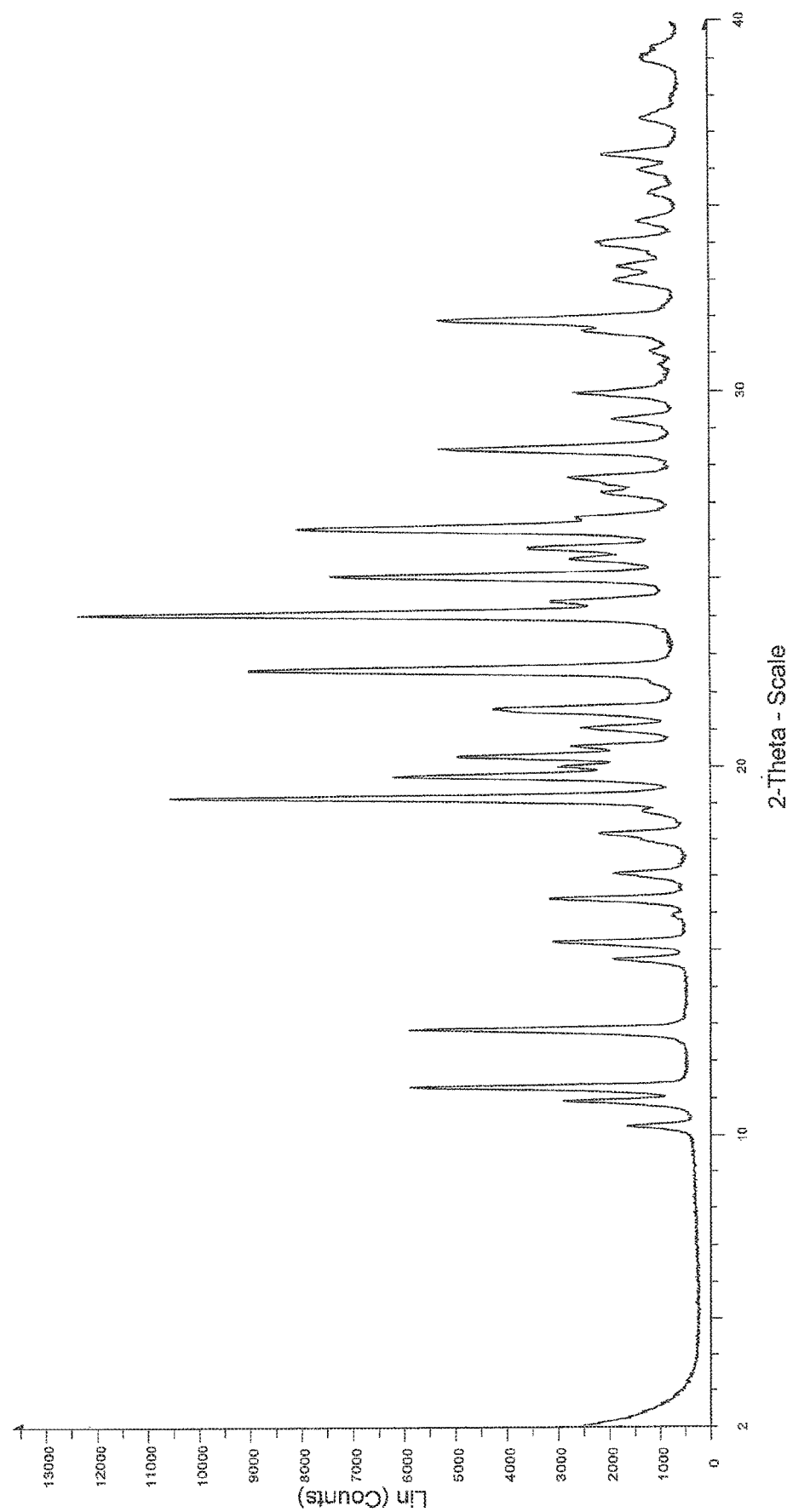
FIG. 1 provides an illustrative XRPD spectrum for the free form of compound of Formula (I), designated herein as Form B, showing degrees 2θ (2-theta) on the X-axis and relative intensity on the Y-axis.

More detailed listings of the XRPD peaks for each of forms B and H$_B$ are set forth in Tables 1 and 2, respectively below, in which the % relative intensity (I/I$_0$×100) is also provided. It should be understood that in the X-ray powder diffraction spectra or pattern that there is inherent variability in the values measured in degrees 2θ (°2θ) as a result of, for example, instrumental variation (including differences between instruments). As such, it should be understood that there is a variability of up to +0.2°2θ in XRPD peak measurements and yet such peak values would still be considered to be representative of a particular solid state form of the crystalline materials described herein. It should also be understood that other measured values from XRPD experiments and DSC/TGA experiments, such as relative intensity and water content, can vary as a result of, for example, sample preparation and/or storage and/or environmental conditions, and yet the measured values will still be considered to be representative of a particular solid state form of the crystalline materials described herein.

DETAILED DESCRIPTION OF THE DISCLOSURE

Definition

As used herein, the terms "about" and "substantially" indicate with respect to features such as endotherms, endothermic peak, exotherms, baseline shifts, etc., that their values can vary. With reference to X-ray diffraction peak positions, "about" or "substantially" means that typical peak position and intensity variability are taken into account. For example, one skilled in the art will appreciate that the peak positions (2θ) will show some inter-apparatus variability, typically as much as 0.2°. Occasionally, the variability could be higher than 0.2° depending on apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only. For DSC, variation in the temperatures observed will depend upon the rate of temperature change as well as sample preparation technique and the particular instrument employed. Thus, the endotherm/melting point values reported herein relating to DSC/TGA thermograms can vary ±5° C. (and still be considered to be characteristic of the particular crystalline form described herein). When used in the context of other features, such as, for example, percent by weight (% by weight), reaction temperatures, the term "about" indicates a variance of ±5%.

The terms "crystalline form(s)" or "crystalline modification(s)" or "polymorphic form(s)" or "polymorph(s)" will be used interchangeably herein As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline. An amorphous solid does not display a definitive X-ray diffraction pattern.

As used herein, "substantially phase pure," when used in reference to any crystalline form of the compound of Formula (I), means a compound having a phase purity of greater than about 90% by weight, including greater than about 90, 91, 92, 93, 94, 95, 96, 97, 98, and about 99% by weight, and also including equal to about 100% by weight of the compound of Formula (I), based on the weight of the compound on an anhydrous basis. The term "phase pure" or "phase purity" herein refers to phase homogeneity with respect to a particular solid state form of the compound of Formula (I) and does not necessarily imply a high degree of chemical purity absent an express statement to that effect. Phase purity may be determined according to methods known in the art, for example, using XRPD to do quantitative phase analysis using one or more approaches known in the art, for example, via an external standard method, direct comparisons of line (peak) characteristics which are attributed to different phases in a particular spectra, or via an internal standard method. However XRPD quantification of phase purity can be complicated by the presence of amorphous material. Accordingly, other methods that may be useful for determining phase purity include, for example, solid state NMR spectroscopy, Raman and/or infrared spectroscopy. One of skilled in the art would readily understand these methods and how to employ these additional (or alternative) methods for determining phase purity.

As used herein, "substantially chemically pure" when used in reference to any crystalline form of the compound of Formula (I), means a compound having a chemical purity greater than about 90% by weight, including greater than about 90, 91, 92, 93, 94, 95, 96, 97, 98, and about 99% by weight, and also including equal to about 100% by weight of the compound of Formula (I), based on the weight of the salt (on an anhydrous basis). The remaining material generally comprises other compounds, such as for example, other stereoisomers of the compound of Formula (I), reaction impurities, starting materials, reagents, side products, and/or other processing impurities arising from the preparation and/or isolation and/or purification of the particular crystalline form. For example, a crystalline form of the compound of Formula (I) may be deemed to be substantially chemically pure if it has been determined to have a chemical purity of greater than about 90% by weight, as measured by standard and generally accepted methods known in the art, where the remaining less than about 10% by weight constitutes other materials such as other stereoisomers of the compound of Formula (I), reaction impurities, starting materials, reagents, side products, and/or processing impurities. Chemical purity may be determined according to methods known in the art, for example, high performance liquid chromatography (HPLC), LC-MS (liquid chromatography-mass spectrometry), nuclear magnetic resonance (NMR) spectroscopy, or infrared spectroscopy. One of skill in the art would readily understand these methods and how to employ these additional (or alternative) methods for determining chemical purity.

As used herein, the term "seed" can be used as a noun to describe one or more crystals of a crystalline compound of Formula (I). The term "seed" can also be used as a verb to describe the act of introducing said one or more crystals of a crystalline compound of Formula (I) into an environment (including, but not limited to e.g., a solution, a mixture, a suspension, or a dispersion) thereby resulting in the formation of more crystals of the crystalline compound of formula (I).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by LTA4H, or (ii) associated with LTA4H activity, or (iii) characterized by activity (normal or abnormal) of LTA4H; or (2) reducing or inhibiting the activity of LTA4H; or (3) reducing or inhibiting the expression of LTA4H. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of LTA4H; or reducing or inhibiting the expression of LTA4H partially or completely.

As used herein, the term "subject" refers to an animal. Preferably, the animal is a mammal. A subject refers to for example, primates (e.g. humans), cows, sheep, goats, horses, dogs, cats, rabbits, rats, mice, fish, birds and the like. In a preferred embodiment, the subject is a human.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

As used herein, the term "inhibit", "inhibition" or "inhibiting" refers to the reduction or suppression of a given condition, symptom, or disorder, or disease, or a significant decrease in the baseline activity of a biological activity or process.

As used herein, the terms "treat," "treating," or "treatment" of any disease or disorder refers in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In one embodiment, "treat" or "treating" refers to delaying the progression of the disease or disorder.

As used herein, the term "prevent", "preventing" or "prevention" of any disease or disorder refers to the prophylactic treatment of the disease or disorder; or delaying the onset of the disease or disorder.

As used herein, a subject is "in need of" or "in need thereof" a treatment if such subject would benefit biologically, medically or in quality of life from such treatment.

The term "comprising" encompasses "including" as well as "consisting"; e.g., a composition comprising X may consist exclusively of X or may include additional, e.g. X and Y.

As used herein the term "combination" refers to either a fixed combination in one dosage unit form, or a combined administration where a crystalline form of compound of Formula (I) and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that a crystalline form of the compound of Formula (I) and a combination partner (i.e. immunotherapeutic agent), are both administered to a patient simultaneously in the form of a single entity or dosage. The term "non-fixed combination" means that a crystalline form of the compound of Formula (I) and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat a LTA4H related disease as described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

Crystalline Forms and Uses

The present disclosure relates to a crystalline form of the free form of (S)-3-amino-4-(5-(4-((5-chloro-3-fluoropyridin-2-yl)oxy)phenyl)-2H-tetrazol-2-yl)butanoic acid (the compound of Formula (I)), which is described and characterized herein.

The present invention also relates to a crystalline form of a hydrate of (S)-3-amino-4-(5-(4-((5-chloro-3-fluoropyridin-2-yl)oxy)phenyl)-2H-tetrazol-2-yl)butanoic acid. More specifically, the present invention relates to a crystalline form a monohydrate of (S)-3-amino-4-(5-(4-((5-chloro-3-fluoropyridin-2-yl)oxy)phenyl)-2H-tetrazol-2-yl)butanoic acid, which is described and characterized herein.

In one embodiment, the present disclosure provides a crystalline form of the free form of (S)-3-amino-4-(5-(4-((5-chloro-3-fluoropyridin-2-yl)oxy)phenyl)-2H-tetrazol-2-yl)butanoic acid (Form B) having an X-ray powder diffraction (XRPD) pattern comprising a representative peak, in terms of °2θ, at 24.1±0.2°2θ measured at a temperature of about 25° C. In another embodiment, the XRPD pattern further comprises one or more additional representative peaks chosen from 22.6±0.2°2θ and 26.3±0.2°2θ. In one aspect of the previous embodiment, the XRPD pattern further comprises one or more additional representative peaks chosen from 11.3 0.2°2θ, 12.8±0.2°2θ, 19.7±0.2°2θ, 25.1±0.2°2θ, and 28.5±0.2°2θ measured at a temperature of about 25° C. Accordingly, the XRPD pattern for the crystalline form of the free form of the compound of Formula (I) may comprise one, two, three, or four representative peaks selected from 11.3±0.2°2θ, 12.8 0.2°2θ, 19.7±0.2°2θ, 22.6±0.2°2θ, 24.1±0.2°2θ, 25.1±0.2°2θ, 26.3±0.2°2θ, and 28.5 0.2°2θ measured at a temperature of about 25° C. In another embodiment, the crystalline form of the free form of the compound of Formula (I) has an XRPD pattern that may further include one or more additional representative peaks chosen from 11.3±0.2°2θ, 12.8±0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0 0.2°2θ, measured at a temperature of about 25° C. Thus, the XRPD pattern for the crystalline form of the free form of the compound of Formula (I) may comprise one or more (e.g. one, two, three, four, five or six) representative peaks selected from 11.3±0.2°2θ, 12.8±0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0 0.2°2θ, measured at a temperature of about 25° C. The XRPD pattern for the crystalline form of the free form of the compound of Formula (I) may comprise one or more (e.g. one, two, three, four, five or six) representative peaks selected from the peaks disclosed in table 1 and measured at a temperature of about 25° C.

In another aspect of the above embodiment, the crystalline form of the free form of compound of Formula (I) is characterized by a x-ray powder diffraction pattern comprising four 2θ values (CuKα λ=1.54184 Å) selected from the group consisting of 11.3±0.2°2θ, 12.8±0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0±0.2°2θ, measured at a temperature of about 25° C.

In another aspect of the above embodiment, the crystalline form of the free form of compound of Formula (I) is characterized by a x-ray powder diffraction pattern comprising five or more 2θ values (CuKα λ=1.54184 Å) selected from the group consisting of 11.3±0.2°2θ, 12.8±0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0±0.2°2θ, measured at a temperature of about 25° C.

In yet another aspect of the above embodiment, the crystalline form of the free form of the compound of Formula (I) has an XRPD pattern substantially as shown in FIG. 1. It should be understood that the water content of Form B can be in the range of about 0% to about 1% and still be considered to be a crystalline form having the XRPD pattern comprising the one, two, three, four, five or six representative peaks described above or in table 1. The water content as determined by Karl Fischer titration method for Form B is 0.1%.

The crystalline form of the free form of (S)-3-amino-4-(5-(4-((5-chloro-3-fluoropyridin-2-yl)oxy)phenyl)-2H-tetrazol-2-yl)butanoic acid may be characterized thermally. In one embodiment, a crystalline form of the free form of the compound of Formula (I) has a thermal profile measured by Differential Scanning Calorimetry (DSC) with a heating rate of 10° C./min comprising a single endothermic peak starting at about 197.4° C. (corresponding to melting under decomposition).

Figure 2:
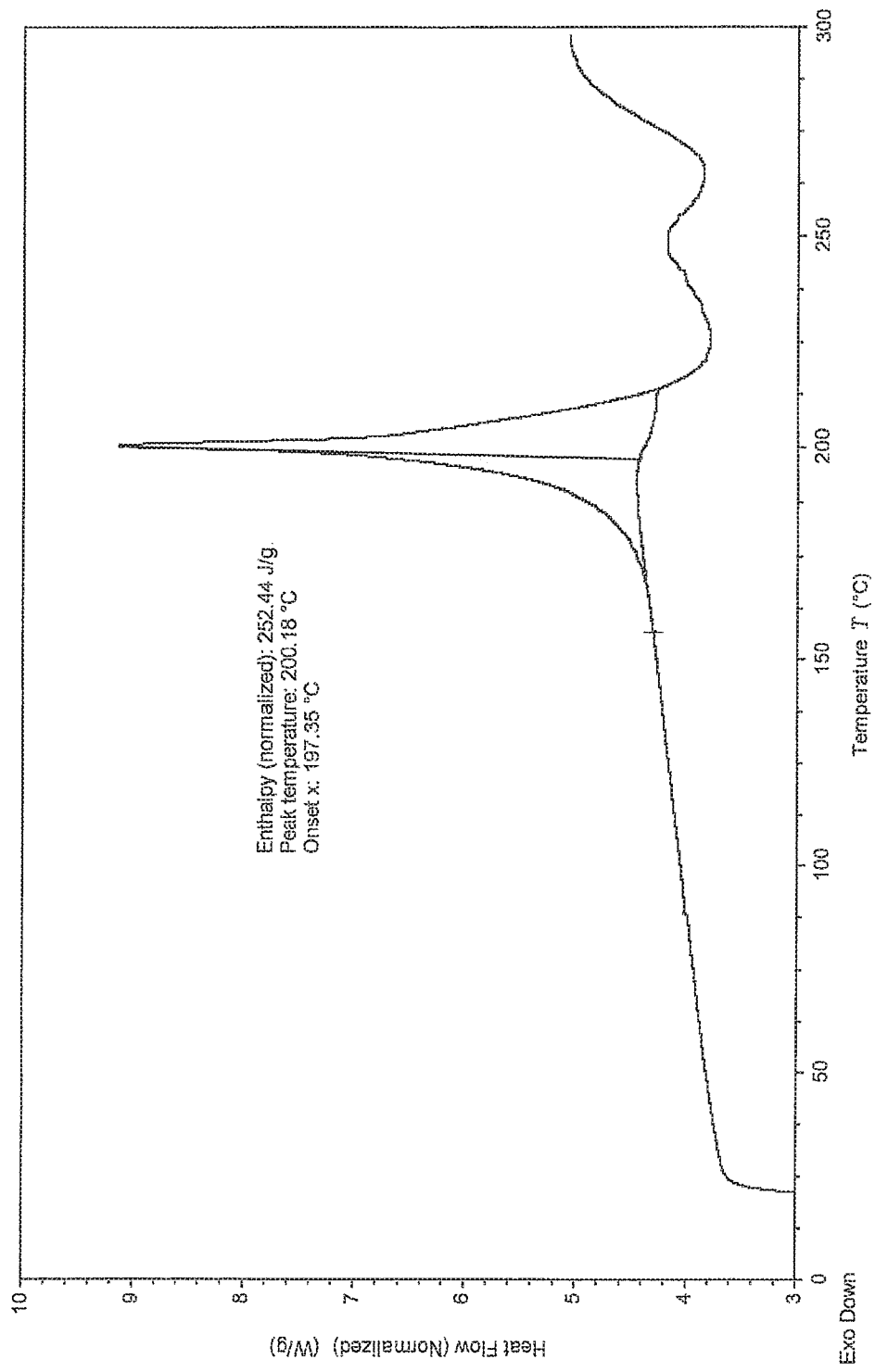
FIG. 2 provides an illustrative DSC for the free form of the compound of Formula (I), designated herein as Form B.

In another embodiment, the crystalline form of the free form of the compound of Formula (I) has a DSC thermogram that is substantially as shown in FIG. 2. It should be understood that hydrated forms may yield different thermograms (in terms of peak shape and profile) depending on instrument parameters, thus the same material may have thermograms that look substantially different from each other when the data is generated on two different instruments.

Figure 3:
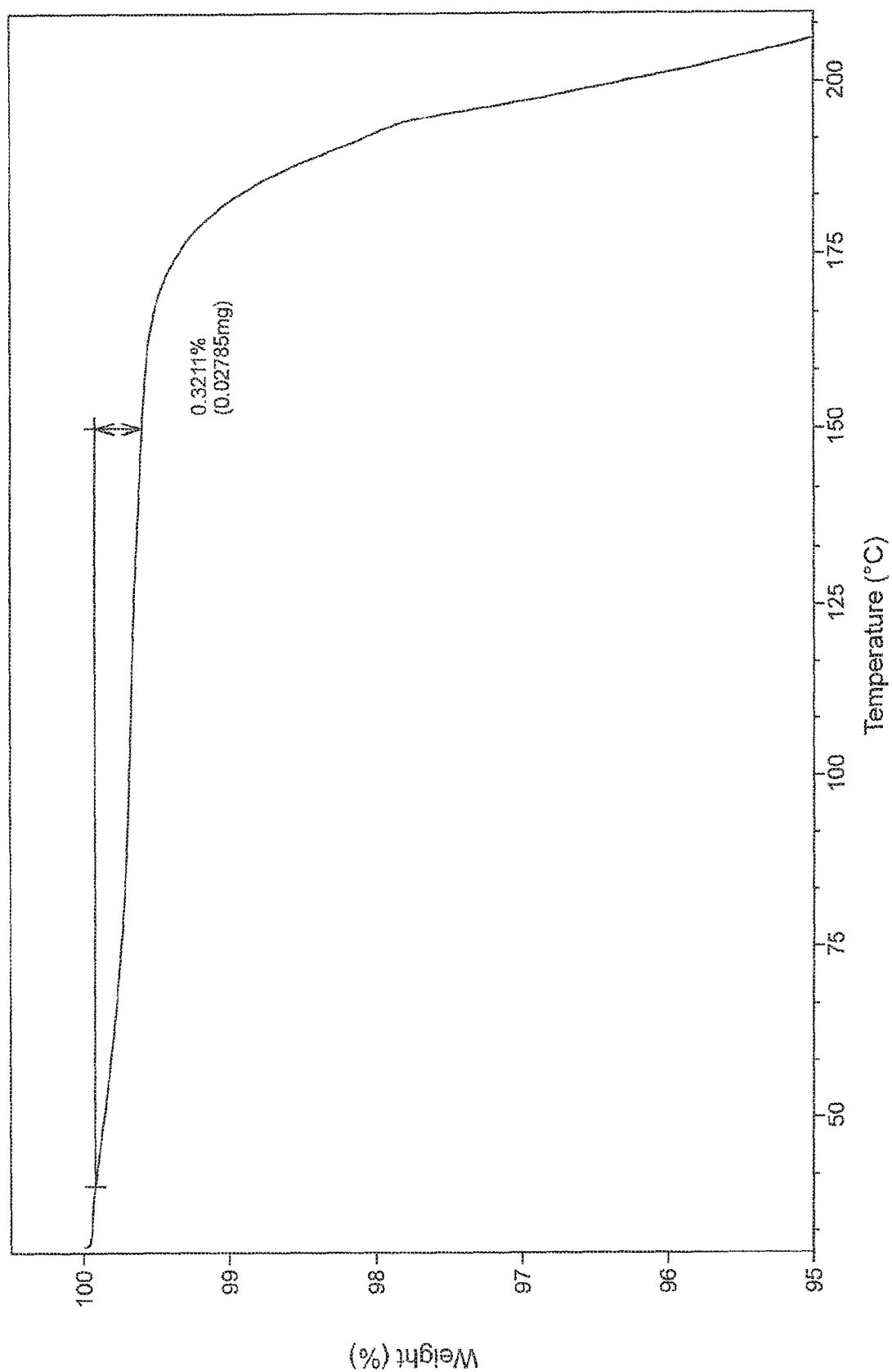
FIG. 3 provides an illustrative TGA for the free form of the compound of Formula (I), designated herein as Form B.

In another embodiment, the crystalline form of the free form of the compound of Formula (I) has a thermogravimetric analysis (TGA) diagram substantially the same as that shown in shown in FIG. 3. The weight loss by TGA is about 0.32% at 150° C.

In yet another embodiment, the crystalline form B is substantially phase pure.

In yet another embodiment, the invention pertains to a process for making crystalline Form B of compound (S)-3-amino-4-(5-(4-((5-chloro-3-fluoropyridin-2-yl)oxy)phenyl)-2H-tetrazol-2-yl)butanoic acid, said process comprises the steps of:
  a) Suspending Form $H_B$ of (S)-3-amino-4-(5-(4-((5-chloro-3-fluoropyridin-2-yl)oxy)phenyl)-2H-tetrazol-2-yl)butanoic acid in alcohol or in a mixture of water/alcohol to form a suspension mixture;
  b) Heating and stirring the suspension mixture to a temperature superior to 50° C.;
  c) Cooling the solution to room temperature to form a suspension mixture;
  d) Collecting crystalline Form B from the suspension mixture.

In yet another embodiment, the process comprises suspending Form $H_B$ of (S)-3-amino-4-(5-(4-((5-chloro-3-fluoropyridin-2-yl)oxy)phenyl)-2H-tetrazol-2-yl)butanoic acid in methanol or in a mixture of water/methanol or in a mixture of water/1-propanol.

In yet another embodiment, the process comprises suspending Form $H_B$ of (S)-3-amino-4-(5-(4-((5-chloro-3-fluoropyridin-2-yl)oxy)phenyl)-2H-tetrazol-2-yl)butanoic acid in methanol.

In yet another embodiment, the process comprises suspending Form $H_B$ of (S)-3-amino-4-(5-(4-((5-chloro-3-fluoropyridin-2-yl)oxy)phenyl)-2H-tetrazol-2-yl)butanoic acid in a mixture of water/1-propanol wherein the ratio water/1-propanol is 30/70% by weight.

In yet another embodiment, the process comprises Suspending Form $H_B$ of (S)-3-amino-4-(5-(4-((5-chloro-3-fluoropyridin-2-yl)oxy)phenyl)-2H-tetrazol-2-yl)butanoic acid in a mixture of water/methanol wherein the ratio water/methanol is from 1:2 to 1:9 volume by volume (v/v). Preferably, the water/methanol ratio is selected from 1:2; 1:4 and 1:9 (v/v). More preferably, the water/methanol ratio is 1:2 v/v.

In yet another embodiment, the temperature used in step b) of the process is preferably superior to 60° C., most preferably superior to 70° C. In a further aspect of this embodiment, the stirring in step b) is more than 24 h, preferably more than 30 h.

In yet another embodiment, the invention pertains to a process for making crystalline Form B of compound (S)-3-amino-4-(5-(4-((5-chloro-3-fluoropyridin-2-yl)oxy)phenyl)-2H-tetrazol-2-yl)butanoic acid, wherein in step d) collecting crystalline form B from the suspension is done by filtration.

In yet another embodiment, the invention pertains to a process for making crystalline Form B of compound (S)-3-amino-4-(5-(4-((5-chloro-3-fluoropyridin-2-yl)oxy)phenyl)-2H-tetrazol-2-yl)butanoic acid, wherein in step d) collecting crystalline form B from the suspension is done by distillation.

The present invention further provides a crystalline form of a hydrate of (S)-3-amino-4-(5-(4-((5-chloro-3-fluoropyridin-2-yl)oxy)phenyl)-2H-tetrazol-2-yl)butanoic acid (Form $H_B$) having an X-ray powder diffraction (XRPD) pattern comprising a representative peak, in terms of °2θ, at 24.7±0.2°2θ, measured at a temperature of about 25° C. In another embodiment, the XRPD pattern further comprises one or more additional representative peaks chosen from 22.1 0.2°2θ, 23.8±0.2°2θ, and 28.7±0.2°2θ, measured at a temperature of about 25° C.

Alternatively, the XRPD pattern for the crystalline form of said hydrate of the compound of Formula (I) may comprise one, two, three, or four representative peaks chosen from 22.1±0.2°2θ, 23.8±0.2°2θ, 24.7±0.2°2θ, and 28.7±0.2°2θ, measured at a temperature of about 25° C.

In another embodiment, the crystalline form of said hydrate of the compound of Formula (I) has an XRPD pattern that may further include one or more additional representative peaks chosen from 13.4±0.2°2θ, 20.8±0.2°2θ, 26.1±0.2°2θ and 33.8±0.2°2θ. Thus, the XRPD pattern for the crystalline form of said hydrate of the compound of Formula (I) may comprise one, two, three, four, five or six representative peaks chosen from 13.4±0.2°2θ, 20.8 0.2°2θ, 22.1±0.2°2θ, 23.8±0.2°2θ, 24.7±0.2°2θ, 26.1±0.2°2θ, 28.7±0.2°2θ and 33.8±0.2°2θ. The XRPD pattern for the crystalline form of the free form of the compound of Formula (I) may comprise one or more (e.g. one, two, three, four, five or six) representative peaks selected from the peaks disclosed in table 2 and measured at a temperature of about 25° C.

In another embodiment, said hydrate form is characterized by a x-ray powder diffraction pattern comprising four or more 2θ values (CuKα λ=1.54184 Å) selected from the group consisting of 13.4±0.2°, 20.8±0.2°, 22.1±0.2°, 23.5±0.2°, 23.5±0.2°, 23.8±0.2, 24.7±0.2°2θ, 26.1±0.2°2θ, 26.9±0.2°2θ, 28.7±0.2°2θ, 30.4±0.2°2θ, 31.2±0.2°2θ, 33.8±0.2°2θ and 38.7±0.2°2θ, measured at a temperature of about 25° C.

In another embodiment, said hydrate form is characterized by a x-ray powder diffraction pattern comprising five or more 2θ values (CuKα λ=1.54184 Å) selected from the group consisting of 13.4±0.2°, 20.8±0.2°, 22.1±0.2°, 23.5±0.2°, 23.5±0.2°, 23.8±0.2, 24.7±0.2°2θ, 26.1±0.2°2θ, 26.9±0.2°2θ, 28.7±0.2°2θ, 30.4±0.2°2θ, 31.2±0.2°2θ, 33.8±0.2°2θ and 38.7±0.2°2θ, measured at a temperature of about 25° C.

Figure 4:
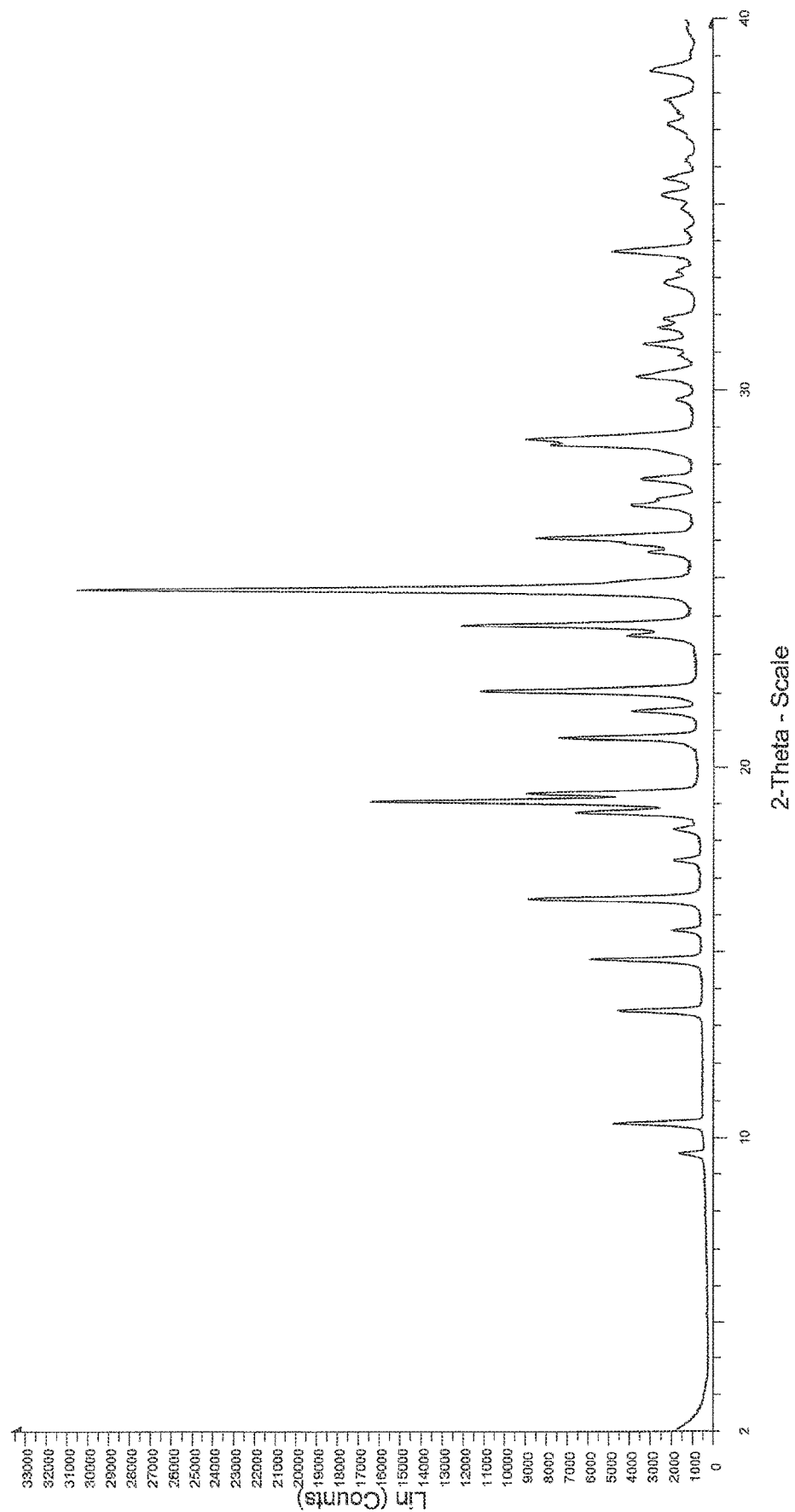
FIG. 4 provides an illustrative XRPD spectrum for a hydrate form of the compound of Formula (I), designated herein as Form H$_B$, showing degrees 2θ (2-theta) on the X-axis and relative intensity on the Y-axis.

In yet another embodiment, a crystalline form of a hydrate of the compound of Formula (I) has an XRPD pattern substantially as shown in FIG. 4. It should be understood that the water content of Form $H_B$ can be in the range of about 2% to about 6% and still be considered to be a hydrate having the XRPD pattern comprising the one, two, three, four, five or six representative peaks described above. The water content as determined by Karl Fischer titration method for Form $H_B$ is 5.1%.

The crystalline form of the hydrate of (S)-3-amino-4-(5-(4-((5-chloro-3-fluoropyridin-2-yl)oxy)phenyl)-2H-tetrazol-2-yl)butanoic acid may be characterized thermally. In one embodiment, a crystalline form of the hydrate of the compound of Formula (I) has a differential thermogravimetric profile comprising an endothermic peak starting at about 95° C. (corresponding to the dehydration) and an endothermic peak starting at about 198.5° C. (corresponding to the melting under decomposition).

Figure 5:
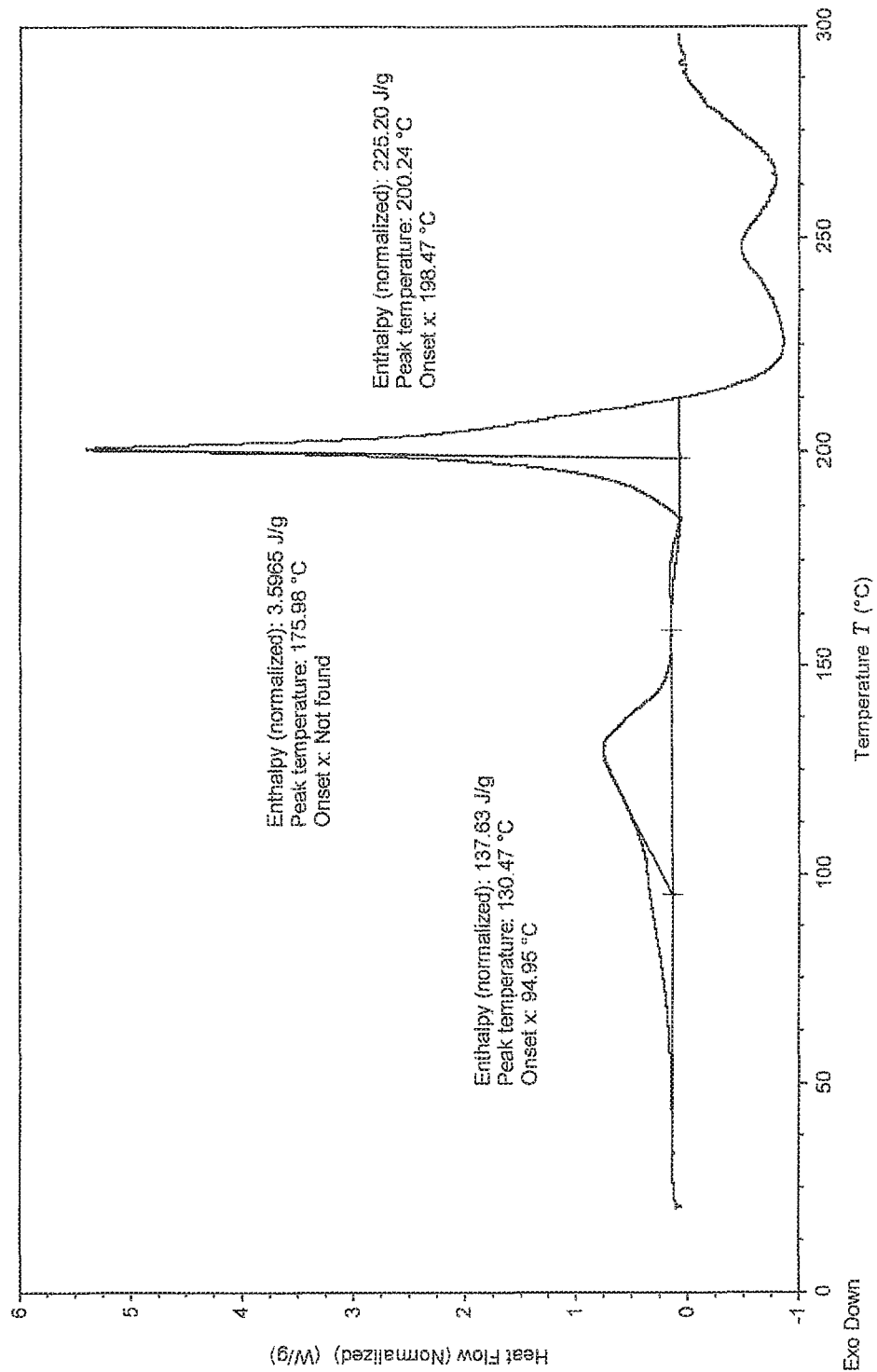
FIG. 5 provides an illustrative DSC for a hydrate form of the compound of Formula (I), designated herein as Form H$_B$.

In another embodiment, a crystalline form of the hydrate of the compound of Formula (I) has a DSC thermogram that is substantially as shown in FIG. 5. It should be understood that hydrated forms may yield different thermograms (in terms of peak shape and profile) depending on instrument parameters, thus the same material may have thermograms that look substantially different from each other when the data is generated on two different instruments.

Figure 6:
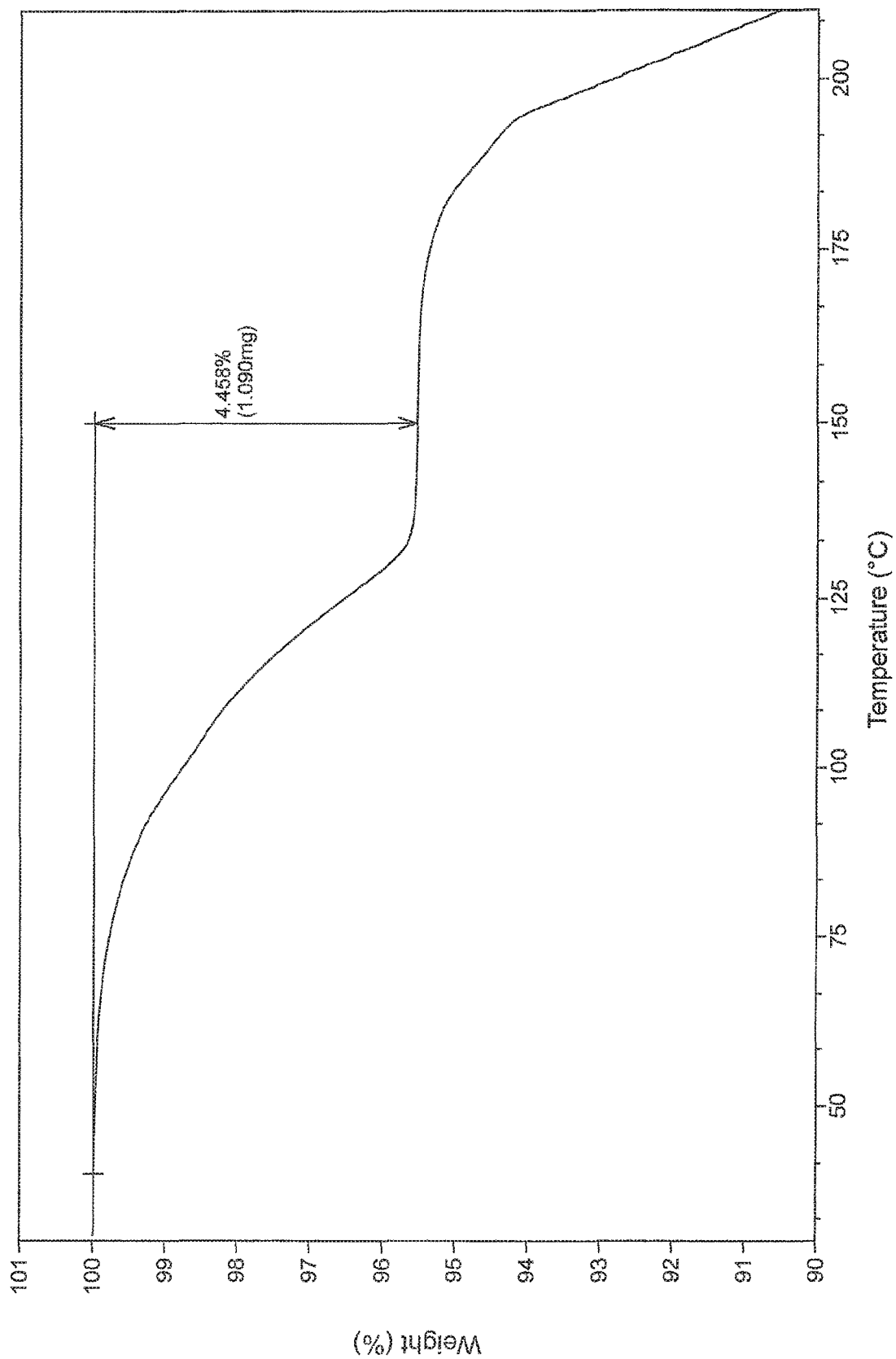
FIG. 6 provides an illustrative TGA for a hydrate form of the compound of Formula (I), designated herein as Form H$_B$.

In another embodiment, a crystalline form of the hydrate of the compound of Formula (I) has a thermo gravimetric analysis (TGA) diagram substantially the same as that shown in shown in FIG. 6. The weight loss by TGA is about 4.46% at 150° C.

In yet another embodiment, the crystalline form $H_B$ described above is a monohydrate form.

In yet another embodiment, the crystalline form $H_B$ is substantially phase pure.

In yet another embodiment, the invention pertains to a process for making crystalline Form $H_B$ of compound (S)-3-amino-4-(5-(4-((5-chloro-3-fluoropyridin-2-yl)oxy)phenyl)-2H-tetrazol-2-yl)butanoic acid, said process comprises the steps of:

a) Dissolving (S)-3-amino-4-(5-(4-((5-chloro-3-fluoropyridin-2-yl)oxy)phenyl)-2H-tetrazol-2-yl)butanoic acid hydrochloride salt in water or in a solvent mixture THF/water to form a solution, b) Adjusting the pH of the solution with an aqueous solution of $NaHCO_3$ or an aqueous solution of NaOH to a pH number between 3.3 and 7.5 while stirring, resulting in a suspension;

c) Collecting the crystalline Form $H_B$ from the suspension.

In a particular aspect of the above embodiment, the invention pertains to a process for making crystalline form $H_B$ wherein in step a), (S)-3-amino-4-(5-(4-((5-chloro-3-fluoropyridin-2-yl)oxy)phenyl)-2H-tetrazol-2-yl)butanoic acid hydrochloride salt is dissolved in water and whether the dilution factor is at least 30 volume per weight. (i.e. 30 volumes of water per weight of compound, e.g. 30 L of water for 1 kg of compound) In another aspect of the above embodiment, the invention pertains to a process for making crystalline form $H_B$ wherein the solvent mixture in step a) is THF/water and whether the dilution factor is at least 15 volumes per weight (i.e. at least 15 volumes of a mixture THF/water per weight of compound; e.g. 15 L of a mixture THF/water per 1 kg of compound). In a particular aspect of this embodiment, the THF/water ratio is about 10:90 (w/w: weight ratio).

In another aspect of the above embodiment, the invention pertains to a process for making crystalline form $H_B$ wherein step a) is performed at room temperature or if necessary at temperature up to 35° C. until a clear solution is obtained.

In yet another embodiment, the invention pertains to a process of making crystalline form $H_B$ wherein in step b) the pH is adjusted to a pH number between 3.3 and 7.5 using an aqueous solution of $NaHCO_3$, preferably a 5-10% w/w aqueous solution of $NaHCO_3$. Preferably the pH is brought to about 4 or about 5.

In yet another embodiment, the invention pertains to a process of making crystalline form $H_B$ wherein in step b) the pH is adjusted to a pH number between 3.3 and 7.5 using an aqueous solution of NaOH, preferably a 32% w/w aqueous solution of NaOH. Preferably the pH is brought to about 4 or about 5.

In yet another embodiment, the invention pertains to a process of making crystalline form $H_B$ wherein in step b) the pH is adjusted to a pH number between 3.3 and 7.5 while stirring and the stirring is continued for up to 20 h.

In yet another embodiment, the invention pertains to a process of making crystalline form $H_B$ wherein in step c), collecting Form $H_B$ from the suspension is performed by filtration.

In yet another embodiment, the invention pertains to a process for making crystalline Form $H_B$ of compound (S)-3-amino-4-(5-(4-((5-chloro-3-fluoropyridin-2-yl)oxy)phenyl)-2H-tetrazol-2-yl)butanoic acid, said process comprises the steps of:
a) Dissolving (S)-3-amino-4-(5-(4-((5-chloro-3-fluoropyridin-2-yl)oxy)phenyl)-2H-tetrazol-2-yl)butanoic acid hydrochloride salt in water or in a solvent mixture THF/water to form a solution,
b) Adjusting the pH of the solution with an aqueous solution of $NaHCO_3$ or an aqueous solution of NaOH to a pH number between 3.3 and 7.5 while stirring, resulting in a suspension;
c) Collecting the crystalline Form $H_B$ from the suspension;
and further comprising the steps d) through i) for making (S)-3-amino-4-(5-(4-((5-chloro-3-fluoropyridin-2-yl)oxy)phenyl)-2H-tetrazol-2-yl)butanoic acid hydrochloride salt;
d) Adding toluene to (S)-3-((tert-butoxycarbonyl)amino)-4-(5-(4-((5-chloro-3-fluoropyridin-2-yl)oxy)phenyl)-2H-tetrazol-2-yl)butanoic acid;
e) Adding an aqueous solution of HCl to form a reaction mixture;
f) Heating and stirring the reaction mixture to a temperature between about 50° C. to about 65° C. optionally under pressure;
g) Cooling down the reaction mixture to about 35° C.,
h) Separating out the aqueous layer and cooling down the resulting organic layer to a temperature between 18° C. and 25° C., resulting in a suspension,
i) Collecting the (S)-3-amino-4-(5-(4-((5-chloro-3-fluoropyridin-2-yl)oxy)phenyl)-2H-tetrazol-2-yl)butanoic acid hydrochloride salt from the suspension.

In on embodiment, the invention pertains to the process of making Form $H_B$ as described above, wherein in step d) toluene is added in a quantity so that the (S)-3-((tert-butoxycarbonyl)amino)-4-(5-(4-((5-chloro-3-fluoropyridin-2-yl)oxy)phenyl)-2H-tetrazol-2-yl)butanoic acid/Toluene ratio is from 1 to 5 to 1 to 10 (weight by weight).

In another embodiment, the invention pertains to the process of making Form $H_B$ as described above, wherein in step e), the aqueous solution of HCl is 30-40% aqueous HCl, preferably about 30% and wherein the amount of HCl is about 15 equivalent of the (S)-3-amino-4-(5-(4-((5-chloro-3-fluoropyridin-2-yl)oxy)phenyl)-2H-tetrazol-2-yl)butanoic acid hydrochloride salt.

In another embodiment, the invention pertains to the process of making Form $H_B$ as described above, wherein step f), is heating the reaction mixture at a temperature between about 60° C. to about 65° C. and stirring for 10-15 h.

In yet another embodiment, the invention pertains to the process of making Form $H_B$ as described above wherein step f) is performed under pressure, i.e. the reactor's releasing pressure was set in order to minimize the amount of HCl escaping the reaction mixture. Preferably, the releasing pressure is set up at about 2000 mbar.

In yet another embodiment, the invention pertains to a process of making crystalline form $H_B$ wherein in step i), collecting (S)-3-amino-4-(5-(4-((5-chloro-3-fluoropyridin-2-yl)oxy)phenyl)-2H-tetrazol-2-yl)butanoic acid hydrochloride salt from the suspension is performed by filtration or by centrifuge.

In another embodiment, the invention relates to a pharmaceutical composition comprising a therapeutically effective amount of a crystalline form of (S)-3-amino-4-(5-(4-((5-chloro-3-fluoropyridin-2-yl)oxy)phenyl)-2H-tetrazol-2-yl)butanoic acid (Form B or Form $H_B$ or a combination thereof), and at least one pharmaceutically acceptable carrier, diluent or excipient. In a particular embodiment, the invention relates to a pharmaceutical composition comprising crystalline form B, and one or more pharmaceutically acceptable carriers, diluents or excipients. In yet another aspect, the invention relates to a pharmaceutical composition comprising crystalline form B in substantially phase pure. In yet another embodiment, the invention relates to a pharmaceutical formulation comprising crystalline form B and further comprising at least one other solid state form of (S)-3-amino-4-(5-(4-((5-chloro-3-fluoropyridin-2-yl)oxy)phenyl)-2H-tetrazol-2-yl)butanoic acid. In one aspect of this embodiment, the other solid state form is crystalline form $H_B$. In yet another embodiment, the other solid state form is an amorphous form of (S)-3-amino-4-(5-(4-((5-chloro-3-fluoropyridin-2-yl)oxy)phenyl)-2H-tetrazol-2-yl)butanoic acid.

In a particular embodiment, the invention relates to a pharmaceutical composition comprising crystalline form JIB, and one or more pharmaceutically acceptable carriers, diluents or excipients. In yet another aspect, the invention relates to a pharmaceutical composition comprising crystalline form $H_B$ in substantially phase pure form. In yet another embodiment, the invention relates to a pharmaceutical composition comprising crystalline form $H_B$ and further comprising at least one other solid state form of (S)-3-amino-4-(5-(4-((5-chloro-3-fluoropyridin-2-yl)oxy)phenyl)-2H-tetrazol-2-yl)butanoic acid. In one aspect of this embodiment, the other solid state form is crystalline form B. In yet another embodiment, the other solid state form is an amorphous form of (S)-3-amino-4-(5-(4-((5-chloro-3-fluoropyridin-2-yl)oxy)phenyl)-2H-tetrazol-2-yl)butanoic acid.

In other embodiments, the invention relates to combinations, in particular pharmaceutical combinations, comprising a therapeutically effective amount of a crystalline form of (S)-3-amino-4-(5-(4-((5-chloro-3-fluoropyridin-2-yl)oxy)phenyl)-2H-tetrazol-2-yl)butanoic acid (Form B, Form $H_B$ or combination thereof), and one or more therapeutic agents.

In a particular embodiment, the invention relates to a pharmaceutical combination comprising crystalline form B, and one or more therapeutic agents. In yet another aspect, the invention relates to a pharmaceutical combination comprising crystalline form B in substantially phase pure from and one or more therapeutic agent. In yet another embodiment, the invention relates to a pharmaceutical combination comprising crystalline form B and further comprising at least one other solid state form of (S)-3-amino-4-(5-(4-((5-chloro-3-fluoropyridin-2-yl)oxy)phenyl)-2H-tetrazol-2-yl)butanoic acid. In one aspect of this embodiment, the other solid state form is crystalline form $H_B$. In yet another embodiment, the other solid state form is an amorphous form of (S)-3-amino-4-(5-(4-((5-chloro-3-fluoropyridin-2-yl)oxy)phenyl)-2H-tetrazol-2-yl)butanoic acid.

In a particular embodiment, the invention relates to a pharmaceutical combination comprising crystalline form $H_B$, and one or more therapeutic agents. In yet another aspect, the invention relates to a pharmaceutical combination comprising crystalline form $H_B$ in substantially phase pure form and one or more therapeutic agent. In yet another embodiment, the invention relates to a pharmaceutical combination comprising crystalline form $H_B$ and further comprising at least one other solid state form of (S)-3-amino-4-(5-(4-((5-chloro-3-fluoropyridin-2-yl)oxy)phenyl)-2H-tetrazol-2-yl)butanoic acid. In one aspect of this embodiment, the other solid state form is crystalline form B. In yet another embodiment, the other solid state form is an amorphous form of (S)-3-amino-4-(5-(4-((5-chloro-3-fluoropyridin-2-yl)oxy)phenyl)-2H-tetrazol-2-yl)butanoic acid.

In another embodiment, the invention provides pharmaceutical combinations as described above wherein the therapeutic agent is independently selected from the group consisting of immunosuppressive or immunomodulating agents or other anti-inflammatory agents. More specifically, the therapeutic agent is selected from the group consisting of a COX inhibitor, a Cysteinyl-Leukotriene Receptor antagonist (including Montelukast, Pranlukast, Zafirlukast), a leukotriene C4 synthase (LTC4S) inhibitor, a statin, sulfasalazine, Mesalamine, a calcineurin inhibitor, e.g. cyclosporin A or FK 506; a mTOR inhibitor, e.g. rapamycin, 40-O-(2-hydroxyethyl)-rapamycin, biolimus-7 or biolimus-9; an ascomycin having immunosuppressive properties, e.g. ABT-281, ASM981; corticosteroids; cyclophosphamide; azathioprene; methotrexate; leflunomide; mizoribine; mycophenolic acid or salt; mycophenolate mofetil; IL-1beta inhibitor.

In one embodiment, the invention relates to a method of treating a diseases or a disorder which is typically ameliorated by the inhibition of LTA4H, in a subject in need thereof, the method comprising: administering to a subject in need thereof, a therapeutically effective amount of a crystalline form of (S)-3-amino-4-(5-(4-((5-chloro-3-fluoropyridin-2-yl)oxy)phenyl)-2H-tetrazol-2-yl)butanoic acid (Form B, Form $H_B$ or a combination thereof), alone or in combination with one or more therapeutic agents.

In another embodiment, the invention relates to a method of treating a disease or a disorder which is typically ameliorated by the inhibition of LTA4H, in a subject in need thereof, comprising administering to said subject, a pharmaceutical composition as described above, alone or in combination with one or more therapeutic agents.

In another embodiment, the invention relates to a method of treating a disease or a disorder which is typically ameliorated by the inhibition of LTA4H, in a subject in need thereof, comprising administering to said subject a pharmaceutical combination as described above.

In one embodiment, the invention relates to the use of a crystalline form of (S)-3-amino-4-(5-(4-((5-chloro-3-fluoropyridin-2-yl)oxy)phenyl)-2H-tetrazol-2-yl)butanoic acid (Form B, Form $H_B$ or a combination thereof), alone or in combination with one or more therapeutic agents, for the treatment of a disease or a disorder which is typically ameliorated by the inhibition of LTA4H.

In yet another embodiment, the invention pertains to a crystalline form of (S)-3-amino-4-(5-(4-((5-chloro-3-fluoropyridin-2-yl)oxy)phenyl)-2H-tetrazol-2-yl)butanoic acid (Form B, Form $H_B$ or a combination thereof), for use in the treatment of a disease or a disorder which is typically ameliorated by the inhibition of LTA4H.

In yet embodiment, the invention pertains to a combination of a crystalline form of (S)-3-amino-4-(5-(4-((5-chloro-3-fluoropyridin-2-yl)oxy)phenyl)-2H-tetrazol-2-yl)butanoic acid (Form B, Form $H_B$ or a combination thereof), and one or more therapeutic agents, for use in the treatment of a disease or a disorder which is typically ameliorated by the inhibition of LTA4H.

In one embodiment, the invention relates to a method of treatment, a use, a compound for use, or a combination for use as described above, wherein the a disease or a disorder which is typically ameliorated by the inhibition of LTA4H is selected from inflammatory and autoimmune disorders and pulmonary and respiratory tract inflammation. More specifically, the disease or the disorder which is typically ameliorated by the inhibition of LTA4H is selected from acute or chronic inflammation, anaphylactic reactions, allergic reactions, atopic dermatitis, psoriasis, acute respiratory distress syndrome, immune complex-mediated pulmonary injury and chronic obstructive pulmonary disease, inflammatory bowel diseases (including ulcerative colitis, Crohn's disease and post-surgical trauma), gastrointestinal ulcers, neutrophilic dermatoses (including but not limited to Pyoderma gangrenosum, Sweet's syndrome, acne and neutrophilic urticaria), immune-complex-mediated glomerulonephritis, autoimmune diseases (including insulin-dependent diabetes mellitus, multiple sclerosis, rheumatoid arthritis, osteoarthritis and systemic lupus erythematosus), vasculitides (including but not limited to cutaneous vasculitis, Behcets disease and Henoch Schonlein Purpura), cardiovascular disorders (including, but not limited to hypertension, atherosclerosis, aneurysm, critical leg ischemia, peripheral arterial occlusive disease, pulmonary artery hypertension and Reynaud's syndrome), sepsis, inflammatory and neuropathic pain including arthritic pain, periodontal disease including gingivitis, ear infections, migraine, benign prostatic hyperplasia, Sjogren-Larsson Syndrome and cancers (including, but not limited to, leukemias and lymphomas, prostate cancer, breast cancer, lung cancer, malignant melanoma, renal carcinoma, head and neck tumors and colorectal cancer). In a preferred embodiment, the disease or the disorder which is typically ameliorated by the inhibition of LTA4H is selected from inflammatory bowel diseases (including ulcerative colitis, Crohn's disease and post-surgical trauma), and neutrophilic dermatoses (including but not limited to Pyoderma gangrenosum, Sweet's syndrome, acne and neutrophilic urticarial).

In one embodiment, the invention relates to the method, the use or the combination for use according to the above embodiment, wherein therapeutic agent is administered together in a single composition or administered separately in two or more different compositions forms.

In one embodiment, the invention pertains to the method, the use or the combination for use as described above wherein the therapeutic agent is administered concurrently with, prior to, or subsequent to, a crystalline form of (S)-3-amino-4-(5-(4-((5-chloro-3-fluoropyridin-2-yl)oxy)phenyl)-2H-tetrazol-2-yl)butanoic acid.

Properties of Crystalline forms of the invention

The crystalline forms described herein have been found to have advantageous properties. The criteria for selection are toxicological considerations, crystallinity, melting point, hygroscopicity, stability in bulk, compatibility with excipients, pH of aqueous solution, solubility in water and aqueous media, morphology, handling and polymorphic behavior. Free form B and hydrate form $H_B$ have demonstrated superior behaviors, especially over the HCl salt which was previously known and described in WO2015/092740. The HCl salt was found to be corrosive, with strong corrosion for steel coupon #1.2767 and moderate corrosion for steel coupon #1.2803 and therefore showed to be inappropriate for further development.

Crystalline form B is an anhydrous form of (S)-3-amino-4-(5-(4-((5-chloro-3-fluoropyridin-2-yl)oxy)phenyl)-2H-tetrazol-2-yl)butanoic acid that is highly crystalline exhibiting columnar habit. It is slightly hygroscopic, with a maximum water uptake of less than 0.7% at 25° C. at 90% RH by DVS.

Crystalline form $H_B$ is a hydrated form of (S)-3-amino-4-(5-(4-((5-chloro-3-fluoropyridin-2-yl)oxy)phenyl)-2H-tetrazol-2-yl)butanoic acid. TGA and DVS data indicate that it is a monohydrate. Crystalline form $H_B$ is not hygroscopic between 10-90% RH but loses his water below 10% RH. Stepwise rehydration to $H_B$ occurs at 10% RH and above 60% RH.

Stability in Solvent:

Equilibrations with solvent were carried out to investigate the relative stability of form $H_B$ in solvent. 50 mg of Form $H_B$ is equilibrated with 1 mL solvent for 24 h (or 7 days, or 28 days) in a water bath at 25° C. or for 7 days at 50° C. The solutions are filtered and dried for 10 minutes in air. The resulting solid is analyzed by XRPD.

Various solvent were investigated: acetone, acetonitrile, dichloromethane, dioxane, ethanol, heptane, methanol, THF, acetone/water mixtures from 10/90 to 90/10, acetonitrile/water mixtures from 10/90 to 90/10, dioxane/water mixtures from 10/90 to 90/10 and ethanol/water mixture from 10/90 to 90/10, tetrahydrofuran/water (50/50) and 1-propanol/water (70/30).

At 25° C. for 7 days or 28 days, Polymorph $H_B$ showed no change in a variety of solvent but converts to amorphous material or gel like material in acetone, dioxane, ethanol, methanol and THF. However, at 50° C. for 7 days, Form $H_B$ became amorphous in many solvents. In methanol, Form $H_B$ transformed into Form B. The transformation of Form $H_B$ to Form B in general occurs at low water content. (Table 3)

TABLE 3

Stability of Form HB in various solvent at 50° C.

| Solvent | Ratio | Solid state residue |
|---|---|---|
| 1,4-Dioxane | — | Amorphous |
| 1-Butanol | — | Amorphous |
| Acetonitrile | — | Amorphous |
| Acetone | — | Amorphous |
| Anisole | — | Amorphous |
| Dichloromethane | — | Amorphous |
| DMSO | — | Amorphous |
| Ethanol | — | Amorphous |
| Ethyl acetate | — | Amorphous |
| Isopropyl acetate | — | Amorphous |
| Isopropanol | — | Amorphous |
| MEK | — | Amorphous |
| Methanol | — | Form B |
| MIBK | — | Amorphous |
| MTBE | — | Amorphous |
| n-Heptane | — | mixture $H_B$ + B |
| NMP | — | Amorphous |
| THF | — | Amorphous |
| Toluene | — | Amorphous |
| Water | — | Form $H_B$ |
| DMSO/water | 90/10 | Amorphous |
| DMSO/water | 50/50 | Form $H_B$ |
| Acetone/water | 90/10 | Form $H_B$ |
| Acetone/water | 50/50 | Form $H_B$ |
| THF/water | 50/50 | Form $H_B$ |
| THF/methanol | 50/50 | Amorphous |
| THF/acetone | 50/50 | Amorphous |
| DMSO/methanol | 50/50 | Amorphous |

Competitive slurry experiments at different water activities at 25° C. and at 50° C. were performed. Competitive slurries of a (1:1) physical mixture of Modifications $H_B$ and B at different water activities were also performed.

TABLE 4

Competitive slurry experiments at different water activities at 25 Degrees Celsius

| | Water activity | Physical mixture of HB and B (1:1) | |
|---|---|---|---|
| | aw | 2 days | 5 days |
| Acetonitrile | 0.00 | Form B | Form B |
| Acetonitrile/water (98:2) | 0.44 | Form B | Form B |
| Acetonitrile/water (97:3) | 0.50 | Forms $H_B$ + B | Form B |
| Acetonitrile/water (92:8) | 0.82 | Forms $H_B$ + B | Forms $H_B$ + B |
| Acetonitrile/water (88:12) | 0.90 | Forms $H_B$ + B | Forms $H_B$ + B |
| Acetonitrile/water (83:17) | 0.93 | Forms $H_B$ + B | Forms $H_B$ + B |
| Water | 1.00 | Forms $H_B$ + B | Forms $H_B$ + B |
| Methanol | 0.00 | Form B | Form B |
| Methanol/water (97:3) | 0.11 | Form B | Form B |
| Methanol/water (89:11) | 0.30 | Form B | Form B |
| Methanol/water (77:23) | 0.50 | Form B | Form B |
| Methanol/water (57:43) | 0.70 | Forms $H_B$ + B | Forms $H_B$ + B |
| Methanol/water (22:78) | 0.90 | Forms $H_B$ + B | Forms $H_B$ + B |

At 25° C. the mixture converted into pure Form B at water activities of aw≤0.5. At water activities above, the mixture remained unchanged. At 50° C. a similar trend could be seen, however, the maximum water activity for transformation to Form B rose to aw≤0.7.

TABLE 4B

Competitive slurry experiments at different water activities at 50 degrees

| | Water activity | Physical mixture of HB and B (1:1) | |
|---|---|---|---|
| | aw | 2 days | 5 days |
| Acetonitrile | 0.00 | Form B | Form B |
| Acetonitrile/water (98:2) | 0.34 | Form B | Form B |
| Acetonitrile/water (97:3) | 0.46 | Form B | Form B |
| Acetonitrile/water (92:8) | 0.77 | Form B | Form B |
| Acetonitrile/water (88:12) | 0.86 | Form B | Form B |
| Acetonitrile/water (83:17) | 0.90 | Forms B + $H_B$ | Form B |
| Water | 1.00 | Forms B + $H_B$ | Forms $H_B$ + B |
| Methanol | 0.00 | Form B | Form B |
| Methanol/water (97:3) | 0.21 | Form B | Form B |
| Methanol/water (89:11) | 0.31 | Form B | Form B |
| Methanol/water (77:23) | 0.51 | Form B | Form B |
| Methanol/water (57:43) | 0.71 | Form B | Form B |
| Methanol/water (22:78) | 0.90 | Forms $H_B$ + B | Forms B + $H_B$ |

It was found that Modification $H_B$ transforms into anhydrous Modification B through slurry in hot or boiling methanol (i.e. a temperature of about 50° C. to about 65° C.). Modification B can be obtained further through high temperature slurry at 80° C. in aqueous solvent mixtures, also from modification $H_B$. Modification B does not transform into other form and is therefore displaying better stability.

Solid State Stability in Bulk and with Excipient Mixtures

The chemical and physical stability of form B and form $H_B$ was investigated, exposing the individual forms to high humidity at temperatures ranging from 25-80° C. Both forms were subject to various test conditions as described below:

Test condition 1: 1 week in a tight container at 80° C., 50° C., 80° C./75% relative humidity (RH) or 50° C./75% RH.

Test condition 2: 1 week in an open container at 80° C.

Test condition 3: 1 week in a tight container at 50° C.

Test condition 4: 1 week in an open container at 50° C./75% RH.

Test condition 5: 1 week in an open container at room temperature/92% RH.

The degradation products were analyzed by HPLC and the sample was analyzed by XPRD to detect any changes to the solid state.

HPLC method:

| Instrument: | Water Acquity UPLC |
|---|---|
| Column: | Water Acquity UPLC BEH shield |
| Particle size (uM): | 1.7 |
| Dimensions (mm): | 2.1 × 100 |
| Temperature (° C.): | 30 |

HPLC method:

| Flow rate (mL/Min): | 0.5 |
|---|---|
| Injection Volume (uL): | 1 |
| Solvent: | Acetonitrile/water (50:50) |
| Concentration (ug/mL): | 500 |
| Detection wavelength (nm): | 248 |
| Mobile Phase A: | 0.1% TFA in acetonitrile/water (5:95) |
| Mobile Phase B: | 0.1% TFA in acetonitrile/water (95:5) |
| Run time (min) | 4 (22) |

| Gradient | % B | Min |
|---|---|---|
| | 0 | Initial |
| | 45 | 15 |
| | 100 | 19 |
| | 100 | 20 |

Under the above described test conditions, form B displayed good stability and did not convert at all. Modification $H_B$ was stable in all conditions except at 80° C. without humidity.

Additionally, Form B was found to be stable upon 1 week at 40° C./90% RH and no hydrate formation was detected. Therefore, form B was identified as the preferred form as it does not hydrate upon exposure to high relative humidity (RH).

Physical Stability

Behavior under compression: The physical stability of crystalline Form $H_B$ was also evaluated. 300 mf of the crystalline form $H_B$ was compressed for 5 minutes at 10 tons with a hydraulic press (diameter of the tablets 13 mm). The sample was then characterized by XRPD to detect any change in the solid state.

No change of crystalline form has been observed by XRPD for crystalline Form $H_B$. Therefore, Crystalline Form $H_B$ was shown to have good physical stability properties.

Behavior under grinding: The physical stability of crystalline form Form $H_B$ was also evaluated. 50 mg of the crystalline form B or $H_B$ were ground manually in a mortar for 3 minutes. Grinding of crystalline form $H_B$ did not result in any change by XRPD.

Behavior under granulation simulation experiment: The physical stability of crystalline forms $H_B$ was also evaluated in granulation simulation experiments. In these experiments granulating solvent was added dropwise to the crystalline form $H_B$ until the solid is wetted sufficiently. The mixture was then vortexed between each addition at 25° C. The mixture was then dried under vacuum. The crystallinity of the material (post-grinding) was re-evaluated by XRPD and/or DSC. The granulating solvent was water or ethanol. Upon granulation using ethanol or water as the granulation solvent, XRPD for polymorph $H_B$ indicated no form change.

Solubility

Form B has a solubility of 0.05 mg/mL at pH values of 4 to 7.

Form B shows a solubility in aqueous buffers in bio-relevant media of 0.07 mg/mL in FaSSIF-V2 (pH=6.6) and of 0.18 mg/mL in FeSSIF-V2 (pH=5.9).

Form $H_B$ has a solubility in aqueous buffers in bio-relevant media of 0.75 mg/mL in simulated gastric fluid (SGF of pH=2); of 0.09 mg/mL in FaSSIF (pH=6.5) and of 0.009 mg/mL in FeSSIF (pH=5.8).

In conclusion, crystalline form B has shown chemical and physical stability in both solution and solid states. Crystalline form $H_B$ is stable over a large humidity range and is highly crystalline but converts to form B in methanol or in aqueous solvent at high temperatures.

Pharmaceutical Composition, Combination, Dosage and Administration

In some embodiments the crystalline forms of (S)-3-amino-4-(5-(4-((5-chloro-3-fluoropyridin-2-yl)oxy)phenyl)-2H-tetrazol-2-yl)butanoic acid described herein can be used alone or they can be formulated into a pharmaceutical composition that also contains at least one pharmaceutically acceptable excipient, and often contains at least two or more pharmaceutically acceptable excipients. Some suitable excipients are disclosed herein. Other excipients may be used that are known in the art without departing from the intent and scope of the present application.

In some embodiments, the present invention utilizes a pharmaceutical composition comprising a compound of the present invention and a pharmaceutically acceptable excipient.

As used herein, the term "pharmaceutically acceptable excipients" includes any and all solvents, carriers, diluents, dispersion media, coatings, surfactants, antioxidants, preservatives (e.g., antibacterial agents, antifungal agents, antioxidants), isotonic agents, absorption delaying agents, salts, drug stabilizers, binders, additives, bulking agents, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). It should be understood that unless a conventional excipient is incompatible with the active ingredient, the use of any conventional excipient in any therapeutic or pharmaceutical compositions is contemplated by the present application.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, carriers or buffering agents, as well as adjuvants, such as solvents, preservatives, stabilizers, wetting agents, emulsifiers and bulking agents, etc.

Typically, the pharmaceutical compositions are tablets or capsules comprising the active ingredient together with at least one excipient, such as:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired;
d) carriers such as an aqueous vehicle containing a co-solvating material such as captisol, PEG, glycerin, cyclodextrin, or the like;
e) disintegrants, e.g., starches, agar, alginic acid or its sodium salt, or effervescent mixtures; and/or
f) absorbents, colorants, flavors and sweeteners.

Tablets may be either film coated or enteric coated according to methods known in the art.

Preferably, the compound or composition is prepared for oral administration, such as a tablet or capsule, for example, and optionally packaged in a multi-dose format suitable for storing and/or dispensing unit doses of a pharmaceutical product. Examples of suitable packaging include, but are not limited to, hermetically sealed foils, unit dose containers (e.g., vials), blister packs, and strip packs.

Tablets may contain the active ingredient in admixture with nontoxic, pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 10-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to the embodiments supra and at least one carrier.

The crystalline forms of (S)-3-amino-4-(5-(4-((5-chloro-3-fluoropyridin-2-yl)oxy)phenyl)-2H-tetrazol-2-yl)butanoic acid as described herein are also useful as active pharmaceutical ingredients (APIs) as well as materials for preparing formulations that incorporate one or more pharmaceutically acceptable excipients and are suitable for administration to human subjects.

Accordingly, in an embodiment of the disclosure, a crystalline form of (S)-3-amino-4-(5-(4-((5-chloro-3-fluoropyridin-2-yl)oxy)phenyl)-2H-tetrazol-2-yl)butanoic acid (Form B or Form $H_B$) is provided in a substantially phase pure form. This crystalline form of a (S)-3-amino-4-(5-(4-((5-chloro-3-fluoropyridin-2-yl)oxy)phenyl)-2H-tetrazol-2-yl)butanoic acid (Form B or Form $H_B$) in substantially phase pure form may be used to prepare pharmaceutical compositions which may further comprising one or more pharmaceutically acceptable excipients. In some embodiments the crystalline form of (S)-3-amino-4-(5-(4-((5-chloro-3-fluoropyridin-2-yl)oxy)phenyl)-2H-tetrazol-2-yl)butanoic acid may not retain its crystallinity in the pharmaceutical composition. For example, in some embodiments crystalline Form B or $H_B$ may be used in a process to prepare a pharmaceutical composition that, for example, involves spray drying or wet granulation; thus it could be that little to no crystalline Form B or $H_B$ is detected in the resulting pharmaceutical composition.

Therapeutic Kits

In one embodiment, the invention provides a kit comprising two or more separate pharmaceutical compositions, at least one of which contains a crystalline form of the compound of formula (I) (Form B or Form $H_B$). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, a crystalline form of a compound of Formula (I) (i.e. Form B or Form $H_B$) and the other therapeutic agent may be manufactured and/or formulated by the same or different manufacturers. Moreover, a crystalline form of the compound of Formula (I) and the other therapeutic may be brought together into a combination therapy: (i) prior to release of the combination product to physicians (e.g. in the case of a kit comprising a crystalline form of compound of Formula (I) and the other therapeutic agent); (ii) by the physician themselves (or under the guidance of the physician) shortly before administration; (iii) in the patient themselves, e.g. during sequential administration of a crystalline form of the compound of Formula (I) and the other therapeutic agent.

Accordingly, the invention provides the use of a crystalline form as described herein (i.e. Form B or Form $H_B$), for treating a disease which is ameliorated by the inhibition of LTA4H (e.g. inflammatory, autoimmune and respiratory diseases), wherein the medicament is prepared for administration with another therapeutic agent. The invention also provides the use of a therapeutic agent for treating a disease which is ameliorated by the inhibition of LTA4H (e.g. inflammatory, autoimmune and respiratory diseases), wherein the medicament is administered with a crystalline form of the compound of Formula (I).

The invention also provides a crystalline form of the compound of Formula (I) (i.e. Form B or Form $H_B$), for use in a method of treating a disease which is ameliorated by the inhibition of LTA4H (e.g. inflammatory, autoimmune and respiratory diseases), wherein the crystalline form of compound of Formula (I) is prepared for administration with another therapeutic agent. The invention also provides another immunotherapeutic agent for use in a method of treating a disease which is ameliorated by the inhibition of LTA4H (e.g. inflammatory, autoimmune and respiratory diseases), wherein the other therapeutic agent is prepared for administration with a crystalline form of compound of Formula (I). The invention also provides crystalline form of compound of Formula (I), for use in a method of treating a disease which is ameliorated by the inhibition of LTA4H (e.g. inflammatory, autoimmune and respiratory diseases), wherein the crystalline form of compound of Formula (I) is administered with another therapeutic agent. The invention also provides another therapeutic agent for use in a method of treating a disease which is ameliorated by the inhibition of LTA4H (e.g. inflammatory, autoimmune and respiratory diseases), wherein the other therapeutic agent is administered with a crystalline form of compound of Formula (I).

The invention also provides the use of a crystalline form of compound of Formula (I), for treating a disease which is ameliorated by the inhibition of LTA4H (e.g. inflammatory, autoimmune and respiratory diseases), wherein the patient has previously (e.g. within 24 hours) been treated with another therapeutic agent. The invention also provides the use of another therapeutic agent for treating a disease which is ameliorated by the inhibition of LTA4H (e.g. inflammatory, autoimmune and respiratory diseases), wherein the patient has previously (e.g. within 24 hours) been treated with a crystalline form of compound of Formula (I).

Combination:

The additional therapeutic agents used in combination with a crystalline form of the invention, include, but are not limited to anti-inflammatory agents, immunomodulatory agents, immunosuppressive agents, or a chemotherapeutic agent.

For example, the compounds of the invention may be used in combination with a COX inhibitor, a Cysteinyl-Leukotriene Receptor antagonist (including Montelukast, Pranlukast, Zafirlukast), a leukotriene C4 synthase (LTC4S) inhibitor, a statin, sulfasalazine, Mesalamine, a calcineurin inhibitor, e.g. cyclosporin A or FK 506; a mTOR inhibitor, e.g. rapamycin, 40-O-(2-hydroxyethyl)-rapamycin, biolimus-7 or biolimus-9; an ascomycin having immunosuppressive properties, e.g. ABT-281, ASM981; corticosteroids; cyclophosphamide; azathioprene; methotrexate; leflunomide; mizoribine; mycophenolic acid or salt; mycophenolate mofetil; IL-1beta inhibitor.

Preparation of Crystalline Form of (S)-3-amino-4-(5-(4-((5-chloro-3-fluoropyridin-2-yl)oxy)phenyl)-2H-tetrazol-2-yl)butanoic acid Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. Exemplary methods of preparing the crystalline forms described herein are set forth in detail below.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Indiana (1999).

For crystallization techniques that employ solvents, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature. This may also be referred to as a suspension.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Alternatively, crystalline forms may be prepared directly from the reaction medium of the final process for preparing (S)-3-amino-4-(5-(4-((5-chloro-3-fluoropyridin-2-yl)oxy)phenyl)-2H-tetrazol-2-yl)butanoic acid. This may be achieved, for example, by employing in the final process step a solvent or a mixture of solvents from which (S)-3-amino-4-(5-(4-((5-chloro-3-fluoropyridin-2-yl)oxy)phenyl)-2H-tetrazol-2-yl)butanoic acid may be crystallized. In addition, crystalline forms may be obtained by distillation or solvent addition techniques.

In addition to the methods discussed briefly below, it should be understood that various analytical methods may be used for the characterization of any of the materials described herein.

The following non-limiting examples are illustrative of the disclosure.

EXAMPLES

Abbreviation

IT: internal temperature
Tj: reactor jacket temperature
Tr: reaction temperature
THF: tetrahydrofuran
Rpm: Revolution per minute Example 1: Preparation of the Crystalline Form $H_B$

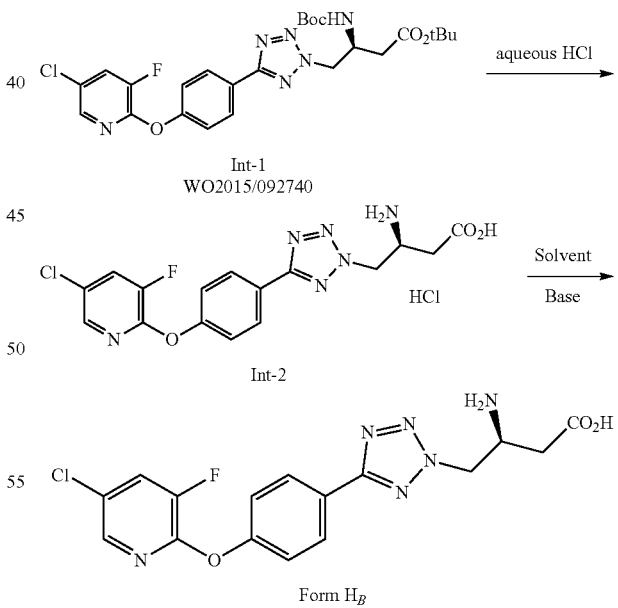

To the 2500 L glass-lined reactor was added Int-1 (55 kg) and toluene (810 kg), and the mixture was stirred (55 rpm, anchor). 31% HCl (232 kg) was added. The releasing pressure of the reactor was set at 2000 mbar. The internal temperature was adjusted 65° C. and stirred (60 rpm) at internal temperature (IT) between 65 and 66° C. for 11 h 29 min. Then the internal temperature was adjusted to 35° C. Then 82 kg of aqueous was separated out under reduced pressure by a Dean-Stark-trap-like equipment ($IT_{max}$=44° C.), and the internal temperature was adjust to ~20. The system was stirred at 19-24° C. for 80 min. The solid was collected by centrifuging. The wet cake was washed by toluene (50 kg with 20 mL antistatic added) and dichloromethane (50 kg). The solid was dried under 195 mbar with JT Baker Sodium bisulfite solution set at 60° C. for 8 h 26 min in titanium tray dryer.

The hydrochloride salt (Int-2) was obtained.

To a 50 L glass-lined reactor was added 5 kg Int-2, and to the reactor was also added 59 kg solvent mixture of THF/water (w/w=7.2/64). The mixture was stirred at 32-34° C. for 2 h (with some insoluble particles observed). The solution was filtered by bag filter and 0.2 μm particle filter consecutively.

The filtrate was transferred to a separate vessel via another 0.2 m particle filter. To the separate vessel was added a solution of $NaHCO_3$ (0.989 kg) in water (15 kg). White solid precipitated out during the addition. After the completion of addition, the solid suspended in the liquid stably, and did not settle down noticeably when stirring stopped. After being stirred at 300 rpm for 67 min, the system was sampled and tested by pH paper, and the result was 4. After being stirred at 300 rpm for 20 hours, the system was filtered. The solid in the filter was washed with 50 kg purified water to yield to Form $H_B$.

Alternatively, Example 29 as described in WO2015/092740 (28 g, 35 mmol) and a solvent mixture containing 360 g water and 40 g THF was mixed together and stirred for 20 minutes. The mixture was filtered and the filtrate was adjusted to pH=5 with aqueous $NaHCO_3$. The stirring was continued for 18 h before the mixture was filtered to afford Polymorph $H_B$ in wet cake 25.6 g, which was used for preparation of polymorph Form B (see example 2) without further purification.

Alternatively, Example 29 as described in WO2015/092740 (15.0 g, 65 mmol, HCl salt) was added to 450 mL water and stirred for 1 hour. The solution was adjusted to pH~4 with aqueous $NaHCO_3$. The mixture was stirred at room temperature for 17 h before filtered. The filter cake was washed with water and dried in vacuo to give 14.7 g of Form $H_B$ which was characterized by XRPD, DSC and TGA (FIGS. 4-6 respectively)

Example 2: Preparation of the Hydrate Crystalline Form B

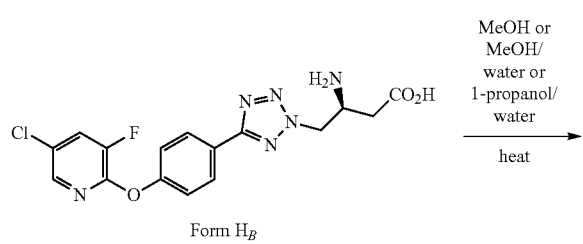

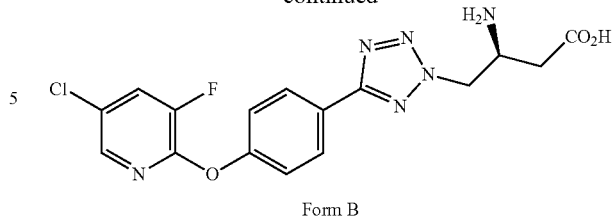

Form B

First method: 505 mg of Form $H_B$ are weighed into a 20 ml glass vial and 6 mL of methanol are added. The slurry is heated to 50° C. and stirred for 4 days using a magnetic stirrer. The suspension is cooled to room temperature and filtered. The recovered solid is dried at 40° C. for 2.5 h under vacuum. The white solid was analyzed by XRPD, DSC and TGA (FIGS. 1-3 respectively).

Second method: Stirring Form $H_B$ in water/MeOH (2:8, 1:9, 1:2 v/v) at a temperature superior to 60° C. would also lead to Form B. For example, 20.7 g Form $H_B$ (dry weight) was added into a premixed solvent mixture containing 810 mL MeOH and 90 mL $H_2O$. The resulting mixture was heated to 68° C. for 36 h before cooling down to 25° C. The mixture was stirred for another 2 h and filtered. The filter cake was dried in vacuo to afford Form B (15.8 g, 76% yield) as a white powder.

M/z=393.1 $[M+H]^+$, Rt=2.47 min (UPLC-MS conditions), Rt=14.85 min (HPLC conditions), $^1H$ NMR (400 MHz, MeOD-$d_4$) δ=8.24 (d, 2H), 7.98 (d, 1H), 7.91 (dd, 1H), 7.36 (d, 2H), 5.17 (d, 2H), 4.25-4.34 (m, 1H), 2.96 (dd, 1H), 2.80 (dd, 1H) ppm, $^{19}F$ NMR (376 MHz, MeOD-$d_4$) δ=−135.7 (d, 1F) ppm For characterization of Form B the following UPLC-MS and HPLC conditions were used: UPLC-MS Conditions: Machine: Waters Acquity UPLC; Column: Waters Aquity BEH C18 (50 mm, internal diameter 2.1 mm, particle size: 1.7 μm); Column temperature: 30° C., Mobile phase (gradient): 0.1% formic acid in water and 0.1% formic acid in acetonitrile (V/V=90/10 to 15/85). Flow rate 0.5 mL/min. Detecting wavelength: 210 nm; HPLC Conditions: Machine: Agilent 1200 HPLC Column: Waters Xbridge C18 (150 mm, internal diameter 3.0 mm, particle size 3.5 μm), Column temperature 30° C.; mobile phase (gradient): 0.1% phosphoric acid in water and acetonitrile (V/V=90/10 to 15/85). Flow rate 0.7 mL/min. Detecting wavelength: 210 nm.

In third method, the starting material Form $H_B$ (1 wt) is charged into a reactor 1 as a suspension in 1-propanol/water 70/30% by weight (41.3 wt) at room temperature. The suspension is heated up to Jacket temperature (Tj)=90° C. ((reaction temperature (Tr)>80° C.) to get complete solubilization. The solution is filtered through pre-heated filtration equipment (filter jacket at 85-90° C.) at 500 mbar pressure and transferred to Reactor 2. The clear filtration is performed by using a Millipore hydrophilic 0.45 um and cellulose Seitz K250P filters. Both filters are pre-wetted with 1-propanol/water 70/30 mixture. The transfer lines and filters are washed by 1-propanol/water 70/30% by weight (4.5 wt) and recombined with the starting material suspension/solution into Reactor 2 (spontaneous solid formation might be observed in the collecting reactor due to temperature drop).

Distillation

The suspension (into Reactor 2) is heated up again to about Tj=85° C. (Tr>80° C.) to get complete solubilization. Once complete solubilization is achieved, the reactor temperature is controlled at 70-75° C. and seed is added (Form B) size reduced seed (0.01 wt) suspended in 1-propanol (0.1 wt). The jacket temperature is heated up to start distillation (at about 80-85° C.) and vacuum is set at 500 mbar. The distillation process starts: internal reactor temperature is controlled between 70-75° C. and vacuum is set at 450-500 mbar. During the distillation process, new 1-propanol solvent (70 wt) is added to replace what distilled away (distillation at constant volume).

At the end of the distillation process, vacuum is released and reactor content is cooled down to 20°. The suspension is sampled for IPC control (water residual amount below 2% wt).

Filtration and Washing

The solid is filtered and washed with 1-propanol (2×10 wt). The solid is characterized by long needle-like shape particles.

The solid is dried at 45-50° C. under vacuum (10-20 mbar residual pressure) under agitation over 24 hours.

Powder X-Ray Diffraction

X-ray powder diffraction (XRPD) patterns were obtained using a Bruker Discovery D8 in reflection geometry. Powders were analyzed using a zero background Si-wafer sample holder. The radiation was Cu Kα (λ=1.5418 Å). Patterns were measured between 2θ and 40° 2theta.

TABLE 1

X-ray powder diffraction data for crystalline hydrate form B

| Angle (°2theta) | Intensity (d value Angstrom) | rel. Intensity (%) |
| --- | --- | --- |
| 10.9 | 2863 | 23 |
| 11.3 | 5874 | 47 |
| 12.8 | 5903 | 48 |
| 15.2 | 3080 | 25 |
| 17.1 | 1900 | 15 |
| 19.7 | 6203 | 50 |
| 20.0 | 2950 | 24 |
| 20.3 | 4949 | 40 |
| 20.5 | 2602 | 21 |
| 21.0 | 2526 | 20 |
| 22.6 | 9030 | 73 |
| 24.1 | 12400 | 100 |
| 24.4 | 3104 | 25 |
| 25.1 | 7318 | 59 |
| 26.3 | 8074 | 65 |
| 28.5 | 5291 | 43 |
| 29.3 | 1891 | 15 |
| 30.0 | 2649 | 21 |
| 36.4 | 2085 | 17 |
| 39.1 | 1308 | 11 |

TABLE 2

X-ray powder diffraction data for crystalline form HB

| Angle (°2theta) | Intensity (d value Angstrom) | rel. Intensity (%) |
| --- | --- | --- |
| 9.5 | 1562 | 5 |
| 13.4 | 4496 | 15 |
| 15.6 | 1945 | 6 |
| 17.4 | 1843 | 6 |
| 20.8 | 7369 | 24 |
| 22.1 | 11139 | 36 |
| 23.5 | 4051 | 13 |
| 23.8 | 12057 | 39 |
| 24.7 | 30575 | 100 |
| 26.1 | 8449 | 28 |
| 26.9 | 3884 | 13 |

TABLE 2-continued

X-ray powder diffraction data for crystalline form HB

| Angle (°2theta) | Intensity (d value Angstrom) | rel. Intensity (%) |
| --- | --- | --- |
| 28.7 | 8930 | 29 |
| 30.4 | 3621 | 12 |
| 31.2 | 3250 | 11 |
| 33.8 | 4785 | 16 |
| 35.7 | 2315 | 8 |
| 37.2 | 2091 | 7 |
| 38.7 | 2926 | 10 |

DSC:

Differential scanning calorimetry was conducted for each crystalline form using a TA Instruments (DSC 2500). For each analysis, 2-4 mg of sample was placed in an aluminium T-zero crucible that closed with a pin-hole lid. The heating rate was 10° C. per minute in the temperature range between 30 and 300° C. Temperatures are reported in degrees Celsius (° C.) and enthalpies are reported in Joules per gram (J/g). Plots are showing endothermic peaks as down. The endothermic melt peak (melting point) was evaluated for extrapolated onset temperature. The accuracy of the measured sample temperature with this method is within about ±1° C., and the heat of fusion can be measured within a relative error of about ±5%.

Illustrative DSC traces generated using crystalline Forms B and $H_B$ are shown in FIGS. 2 and 4, respectively.

Form B: Melting endotherm: Tonset=197.4° C. (melting under decomposition)

Form $H_B$: Melting endotherm: Tonset=95° C. (dehydration) and Tonset=198.5° C. (melting under decomposition)

Thermogravimetric Analysis (TGA):

TGA curves were obtained using a TA-instrument Q5000. 5-15 mg of sample was placed into an aluminum crucible and sealed hermetically. The sealed crucible was pierced by the robotic auto sampler immediately before analysis. The TGA curve was measured at 10° C./min between 30-300° C. The LoD (Loss of drying) was calculated between 40° C. and 150° C. The weight loss is plotted against the measured sample temperature. Temperatures are reported in degrees Celsius (° C.) and weight loss in %.

Illustrative TGA traces generated using crystalline Forms B and $H_B$ are shown in FIGS. 3 and 6, respectively.

What is claimed is:

1. A crystalline form B of the compound (S)-3-amino-4-(5-(4-((5-chloro-3-fluoropyridin-2-yl)oxy)phenyl)-2H-tetrazol-2-yl)butanoic acid in its free form, characterized by one of the following characteristics:
   (i) an x-ray powder diffraction pattern comprising representative peaks in terms of 2θ at 22.6±0.2°2θ, 24.1±0.2°2θ and 26.3±0.2°2θ, measured at a temperature of about 25° C. and an x-ray wavelength, λ, of 1.5418 Å;
   (ii) an x-ray powder diffraction pattern comprising four or more 2θ values selected from the group consisting of 11.3±0.2°2θ, 12.8 0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0±0.2°2θ, measured at a temperature of about 25° C. and an x-ray wavelength, λ, of 1.5418 Å; and
   (iii) an x-ray powder diffraction pattern comprising five or more 2θ values selected from the group consisting of 11.3±0.2°2θ, 12.8 0.2°2θ, 15.2±0.2°2θ, 19.7±0.2°2θ, 20.0±0.2°2θ, 20.3±0.2°2θ, 21.0±0.2°2θ, 22.6±0.2°2θ, 24.1±0.2°2θ, 24.4±0.2°2θ, 25.1±0.2°2θ, 26.3±0.2°2θ, 28.5±0.2°2θ, and 30.0±0.2°2θ, measured at a temperature of about 25° C. and an x-ray wavelength, λ, of 1.5418 Å.

2. The crystalline form according to claim 1 having an x-ray diffraction spectrum substantially the same as the x-ray powder diffraction spectrum shown in FIG. 1.

3. The crystalline form according to claim 1 having a differential scanning calorimetry (DSC) thermogram substantially the same as that shown in shown in FIG. 2.

4. The crystalline form according to claim 1 having a thermo gravimetric analysis (TGA) diagram substantially the same as that shown in shown in FIG. 3.

5. The crystalline form according to claim 1 consisting essentially of Form B.

6. The crystalline form according to claim 1, wherein Form B is in a substantially phase pure form.

7. A crystalline form $H_B$ of a hydrate of the compound (S)-3-amino-4-(5-(4-((5-chloro-3-fluoropyridin-2-yl)oxy)phenyl)-2H-tetrazol-2-yl)butanoic acid in its free form, characterized by one of the following characteristics:
  (i) an x-ray powder diffraction pattern comprising representative peaks in terms of 2θ at 22.1±0.2°2θ, 23.8±0.2°2θ, 24.7±0.2°2θ and 28.7±0.2°2θ, measured at a temperature of about 25° C. and an x-ray wavelength, λ, of 1.5418 Å;
  (ii) an x-ray powder diffraction pattern comprising four or more 2θ values selected from the group consisting of 13.4±0.2°, 20.8±0.2°, 22.1±0.2°, 23.5±0.2°, 23.5±0.2°, 23.8±0.2, 24.7±0.2°2θ, 26.1±0.2°2θ, 26.9±0.2°2θ, 28.7±0.2°2θ, 30.4±0.2°2θ, 31.2±0.2°2θ, 33.8±0.2°2θ and 38.7±0.2°2θ, measured at a temperature of about 25° C. and an x-ray wavelength, λ, of 1.5418 Å; and
  (iii) an x-ray powder diffraction pattern comprising five or more 2θ values selected from the group consisting of 13.4±0.2°, 20.8±0.2°, 22.1±0.2°, 23.5±0.2°, 23.5±0.2°, 23.8±0.2, 24.7±0.2°2θ, 26.1±0.2°2θ, 26.9±0.2°2θ, 28.7±0.2°2θ, 30.4±0.2°2θ, 31.2±0.2°2θ, 33.8±0.2°2θ and 38.7±0.2°2θ, measured at a temperature of about 25° C. and an x-ray wavelength, λ, of 1.5418 Å.

8. The crystalline form according to claim 7 having a X-ray diffraction spectrum substantially the same as the X-ray powder diffraction spectrum shown in FIG. 4.

9. The crystalline form according to claim 7 having a differential scanning calorimetry (DSC) thermogram substantially the same as that shown in shown in FIG. 5.

10. The crystalline form according to claim 7 having a thermo gravimetric analysis (TGA) diagram substantially the same as that shown in shown in FIG. 6.

11. The crystalline form according to claim 7 wherein said hydrate is a monohydrate.

12. The crystalline form according to claim 7 consisting essentially of Form $H_B$.

13. The crystalline form according to claim 7 wherein Form $H_B$ is in a substantially phase pure form.

14. A pharmaceutical composition comprising a crystalline form selected from the group consisting of Form B according to claim 1, Form $H_B$ according to claim 7; and combinations of Forms B and $H_B$; and one or more pharmaceutically acceptable excipients.

15. A pharmaceutical composition comprising a crystalline form selected from the group consisting of Form B according to claim 1, Form $H_B$ according to claim 7; and combinations of Forms B and $H_B$; in combination with one or more therapeutic agents, wherein the therapeutic agent is independently selected from the group consisting of a COX inhibitor, a Cysteinyl-Leukotriene Receptor antagonist, a leukotriene C4 synthase (LTC4S) inhibitor, a statin, sulfasalazine, Mesalamine, a calcineurin inhibitor; a mTOR inhibitor; an ascomycin having immunosuppressive properties; corticosteroids; cyclophosphamide; azathioprene; methotrexate; leflunomide; mizoribine; mycophenolic acid or salt; mycophenolate mofetil; IL-1beta inhibitor.

16. A method of treating an inflammatory or autoimmune disease or a disorder, in a subject in need thereof, comprising administering to the mammal a therapeutically-effective amount of a crystalline form selected from the group consisting of Form B according to claim 1, Form $H_B$ according to claim 7; and combinations of Forms B and $H_B$.

* * * * *